US012042517B2

(12) United States Patent
Jin

(10) Patent No.: US 12,042,517 B2
(45) Date of Patent: *Jul. 23, 2024

(54) NUCLEIC ACID SYSTEMS THAT ENABLE BACTERIA TO SPECIFICALLY TARGET SOLID TUMORS VIA GLUCOSE-DEPENDENT VIABILITY

(71) Applicant: New Portal Limited, Hong Kong (CN)

(72) Inventor: Ye Jin, Hong Kong (CN)

(73) Assignee: NEW PORTAL LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/661,288

(22) Filed: Apr. 28, 2022

(65) Prior Publication Data

US 2022/0273730 A1    Sep. 1, 2022

Related U.S. Application Data

(62) Division of application No. 16/644,940, filed as application No. PCT/CN2017/101069 on Sep. 8, 2017, now Pat. No. 11,458,172.

(51) Int. Cl.
| | |
|---|---|
| *A61K 35/74* | (2015.01) |
| *A61P 35/00* | (2006.01) |
| *C07K 14/245* | (2006.01) |
| *C12N 15/63* | (2006.01) |
| *C12N 15/70* | (2006.01) |

(52) U.S. Cl.
CPC .............. *A61K 35/74* (2013.01); *A61P 35/00* (2018.01); *C07K 14/245* (2013.01); *C12N 15/635* (2013.01); *C12N 15/70* (2013.01); *C12N 2810/55* (2013.01)

(58) Field of Classification Search
CPC ....... A61K 35/74; A61P 35/00; C07K 14/245; C12N 15/635; C12N 15/70; C12N 2810/55; C12N 1/20; C12N 15/63; Y02A 50/30
See application file for complete search history.

(56) References Cited

U.S. PATENT DOCUMENTS

| | | | |
|---|---|---|---|
| 5,478,804 | A | 12/1995 | Calabresi et al. |
| 6,645,490 | B2 | 11/2003 | Yarkoni et al. |
| 9,198,950 | B2 | 12/2015 | Mellata |
| 9,555,127 | B2 | 1/2017 | Cueva-Méndez |
| 9,889,164 | B2 | 2/2018 | Falb et al. |
| 11,696,931 | B2 * | 7/2023 | Jin ...................... C07K 14/245 424/93.2 |
| 2018/0325963 | A1 | 11/2018 | Isabella et al. |
| 2020/0323926 | A1 | 10/2020 | Jin |

FOREIGN PATENT DOCUMENTS

| | | |
|---|---|---|
| CN | 1055879 A | 11/1991 |
| CN | 1420783 A1 | 5/2003 |
| CN | 1688699 A | 10/2005 |
| CN | 101010002 A1 | 8/2007 |
| CN | 104498418 A | 4/2015 |
| CN | 105483067 A | 4/2016 |
| CN | 106676119 A | 5/2017 |
| CN | 107636146 A | 1/2018 |
| CN | 110527655 A | 12/2019 |
| CN | 111246865 A1 | 6/2020 |
| CN | 111315868 A | 6/2020 |
| EP | 2543720 A1 | 1/2013 |
| IN | 201403506 I3 | 7/2016 |
| TW | 201206472 A | 2/2012 |
| WO | 9958652 A2 | 11/1999 |
| WO | 9958652 A3 | 1/2000 |
| WO | 2001005421 A1 | 1/2001 |
| WO | 2009098246 A1 | 8/2009 |
| WO | 2012087483 A1 | 6/2012 |
| WO | 2016106343 A1 | 6/2016 |
| WO | 2016141108 A1 | 9/2016 |
| WO | 2016183531 A1 | 11/2016 |
| WO | 2016185471 A1 | 11/2016 |
| WO | 2016210373 A2 | 12/2016 |
| WO | 2015118541 A1 | 7/2020 |
| WO | 2020151185 A1 | 7/2020 |

OTHER PUBLICATIONS

Whisstock et al. Quaterly Reviews of Biophysics, 2003, "Prediction of protein function from protein sequence and structure", 36(3):307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10: 8-9. (Year: 2002).*

Engelbart, K. & Gericke, D. (1964). Oncolysis by Clostridia. V. Transplanted Tumors of the Hamster. Cancer Res 24, 239-242.

(Continued)

*Primary Examiner* — Iqbal H Chowdhury
(74) *Attorney, Agent, or Firm* — EAGLE IP LIMITED

(57) ABSTRACT

Provided is a nucleic acid system introduced into a bacterial strain to generate a genetically engineered bacterial strain that grows in solid tumors but does not grow in non-tumor tissues, the nucleic acid system comprising: a first DNA fragment that encodes a toxin gene that expresses a toxin that kills the genetically engineered bacterial strain; a second DNA fragment that encodes an antidote gene that expresses an antidote that negates the toxin; a first promotor that controls transcription of the antidote gene, such that glucose represses the transcription of the antidote gene; and a first constitutive promoter that causes constitutive expression of the toxin gene; wherein the second DNA fragment is transcribed in the solid tumors but not transcribed in the non-tumor tissues.

15 Claims, 13 Drawing Sheets

Specification includes a Sequence Listing.

(56) References Cited

OTHER PUBLICATIONS

Thiele, E. H., Arison, R. N. & Boxer, G. E. (1964). Oncolysis by Clostridia. IV. Effect of Nonpathogenic Clostridial Spores in Normal and Pathological Tissues. Cancer Res 24, 234-238.
Sasaki, T. et al. (2006). Genetically engineered Bifidobacterium longum for tumor-targeting enzyme-prodrug therapy of autochthonous mammary tumors in rats. Cancer science 97, 649-657.
Yazawa, K. et al. (2001). Bifidobacterium longum as a delivery system for gene therapy of chemically induced rat mammary tumors. Breast Cancer Res Treat 66, 165-170.
Lee, C. H., Wu, C. L. & Shiau, A. L. (2008). *Salmonella choleraesuis* as an anticancer agent in a syngeneic model of orthotopic hepatocellular carcinoma. Int J Cancer 122, 930-935.
Pawelek, J. M., Low, K. B. & Bermudes, D. (1997). Tumor-targeted *Salmonella* as a novel anticancer vector. Cancer Res 57, 4537-4544.
Sznol, M., Lin, S. L., Bermudes, D., Zheng, L. M. & King, I. (2000). Use of preferentially replicating bacteria for the treatment of cancer. J Clin Invest 105, 1027-1030.
Cronin, M. et al. (2012). High resolution in vivo bioluminescent imaging for the study of bacterial tumour targeting. PLoS One 7, e30940.
Stritzker, J. et al. (2007). Tumor-specific colonization, tissue distribution, and gene induction by probiotic *Escherichia coli* Nissle 1917 in live mice. International journal of medical microbiology : IJMM 297, 151-162.
Krick, E. L. et al. (2012). Evaluation of Clostridium novyi-NT spores in dogs with naturally occurring tumors. American journal of veterinary research 73, 112-118.
Roberts, N. J. et al. (2014). Intratumoral injection of Clostridium novyi-NT spores induces antitumor responses. Science translational medicine 6, 249ra111.
Min, J. J. et al. (2008). Noninvasive real-time imaging of tumors and metastases using tumor-targeting light-emitting *Escherichia coli*. Molecular imaging and biology : MIB : the official publication of the Academy of Molecular Imaging 10, 54-61.
Yu, B. et al. (2012). Explicit hypoxia targeting with tumor suppression by creating an "obligate" anaerobic *Salmonella typhimurium* strain. Sci Rep 2, 436.
Frahm, M. et al. (2015). Efficiency of conditionally attenuated *Salmonella enterica* serovar Typhimurium in bacterium-mediated tumor therapy. mBio 6(2):e00254-15.
Stern, C. et al. (2015). Induction of CD4(+) and CD8(+) anti-tumor effector T cell responses by bacteria mediated tumor therapy. Int J Cancer 137, 2019-2028.
Hirayama, A. et al. (2009). Quantitative metabolome profiling of colon and stomach cancer microenvironment by capillary electrophoresis time-of-flight mass spectrometry. Cancer Res 69, 4918-4925.
Urasaki, Y., Heath, L. & Xu, C. W. (2012). Coupling of glucose deprivation with impaired histone H2B monoubiquitination in tumors. PLoS One 7, e36775.
Jacob, F. & Monod, J. (1961). Genetic regulatory mechanisms in the synthesis of proteins. J Mol Biol 3, 318-356.
Afif, H., Allali, N., Couturier, M. & Van Melderen, L. (2001). The ratio between CcdA and CcdB modulates the transcriptional repression of the ccd poison-antidote system. Mol Microbiol 41, 73-82.
Zhao, M. et al. (2005). Tumor-targeting bacterial therapy with amino acid auxotrophs of GFP-expressing *Salmonella yphimurium*. Proc Natl Acad Sci U S A 102, 755-760.
Diaz, L. A., Jr. et al. (2005). Pharmacologic and toxicologic evaluation of C. novyi-NT spores. Toxicological sciences : an official journal of the Society of Toxicology 88, 562-575.
Z. Douvlis. (1999) Interference of amino acid patterns and tissue-specific amino acids absorption dominance under the influence of tumor cell protein degradation toxins Medical Hypotheses No. 53 (5), 450-457.
Guillermo De La Cueva-Mendez et al. (2003) Regulatable killing of eukaryotic cells by the prokaryotic proteins Kid and Kis The EMBO Journal No. 22 (2), 246-251.

Lukasz Wieteska et al. (2014)Toxins VapC and PasB from prokaryotic TA modules remain active in mammalian cancer cells Toxins No. 6, 2948-2931.
Yeo, Chewchieng et al.(2016) Heterologous expression of toxins from bacterial Toxin-Antitoxin Systems in eukaryotic cells: strategies and applications Toxins No. 49 (8), 1-16.
Smith, M.A., et al. (2015). Antibodies against hemolysin and cytotoxic necrotizing factor type 1 (CNF1) reduce pladder inflammation in a mouse model of urinary tract infection with toxigenic uropathogenic *Escherichia coli*. Infect Immun 83, 1661-1673.
Zhao, M., et al. (2006). Targeted therapy with a *Salmonella typhimurium* leucine-arginine auxotroph cures orthotopic human breast tumors in nude mice. Cancer Res 66, 7647-7652.
Fensterle J et al. (2008) Cancer immunotherapy based on recombinant *Salmonella enterica* serovar Typhimurium aroA strains secreting prostate-specific antigen and cholera toxin subunit B. Cancer Gene Ther. Feb. 15(2):85-93.
Shimazu T, et al. (2014) Regression of solid tumors by induction of MazF, a bacterial mRNA endoribonuclease. J Mol Microbiol Biotechnol. 24(4):228-33.
Bakhtiari R, et al. (2016) Rising Cellular Immune Response after Injection of pVax/iutA: A Genetic DNA Cassette as Candidate Vaccine against Urinary Tract Infection. Iran J Public Health. 45(7):890-6.
Goodall Eca, et al. (2018) The Essential Genome of *Escherichia coli* K-12. mBio. Feb. 20, 2018;9(1):e02096-17.
Habibi M, et al. (2017) Evaluation of prevalence, immunogenicity and efficacy of FyuA iron receptor in uropathogenic *Escherichia coli* isolates as a vaccine target against urinary tract infection. Microb Pathog. Sep; 110:477-483.
Hur J, et al. (2017) Ontology-based literature mining of *E. coli* vaccine-associated gene interaction networks. J Biomed Semantics. Mar. 14;8(1):12.
Jiang, S.N., et al. (2010). Inhibition of tumor growth and metastasis by a combination of *Escherichia coli*-mediated cytolytic therapy and radiotherapy. Molecular therapy : the journal of the American Society of Gene Therapy 18, 635-642.
Leventhal, D.S, et al. (2020). Immunotherapy with engineered bacteria by targeting the STING pathway for anti-tumor immunity. Nature communications 11, 2739.
Nichols, K.B., et al. (2016). Molecular Characterization of the Vacuolating Autotransporter Toxin in Uropathogenic *Escherichia coli*. J Bacteriol 198, 1487-1498.
Quispe-Tintaya, W., et al.(2013). Nontoxic radioactive Listeria(at) is a highly effective therapy against metastatic pancreatic cancer. Proc Natl Acad Sci U S A 110, 8668-8673.
The Present Study Situation on the Application of Staphylococcal Enterotoxin B (SEB)in Tumor Therapy, (2002) Journal of Microbiology July vol. 22 No. 4.
Jin M., (2000) "Tumor-targeted bacterial as a novelanti-cancer vector" China Biotechnology 20.2 : 49-51.
Olivier Epaulard, et al. (2008) Optimization of a type III secretion system-based Pseudomonas aeruginosa live vector for antigen delivery. Clinical and Vaccine Immunology, American Society for Microbiology, 5 (2), pp. 308-313.
Forbes N. S. (2010). Engineering the perfect (bacterial) cancer therapy. Nature reviews. Cancer, 10(11), 785-794.
Gazit, G., Hung, G., Chen, X., Anderson, W. F., & Lee, A. S. (1999). Use of the glucose starvation-inducible glucose-regulated protein 78 promoter in suicide gene therapy of murine fibrosarcoma. Cancer research, 59(13), 3100-3106.
Jean, A. T. S., Swofford, C. A., Panteli, J. T., Brentzel, Z. J., & Forbes, N. S. (2014). Bacterial delivery of *Staphylococcus aureus* α-hemolysin causes regression and necrosis in murine tumors. Molecular Therapy, 22(7), 1266-1274.
John F. Toso; et al., Phase I Study of the Intravenous Administration of Attenuated *Salmonella typhimurium* to Patients With Metastatic Melanoma, J Clin Oncol., Jan. 1, 2002, 142-152, 20(1), NIH Public Access.
Christopher Groth; et al., Immunosuppression mediated by myeloid-derived suppressor cells (MDSCs) during tumour progression, British Journal of Cancer, 2019, 16-25; 120, Cancer Research UK.

(56) References Cited

OTHER PUBLICATIONS

Dmitry I. Gabrilovich; et al., Coordinated regulation of myeloid cells by tumours, Nat Rev Immunol. Apr. 1, 2013, 253-268, 12(4), NIH Public Access.

J. Martin Brown, Tumor Microenvironment and the Response to Anticancer Therapy, Cancer Biology & Therapy, Aug. 13, 2002, 453-458, 1:5, Landes Bioscience.

Hyun Min Jeon; et al., Early growth response 1 regulates glucose deprivation-induced necrosis, Oncology Reports, 2013, 669-675, 29.

Whisstock J; et al., Prediction of protein function from protein sequence and structure, Quarterly Reviews of Biophysics, Aug. 2003, 307-340, 36(3), Cambridge University Press London.

Andrzej Witkowski; et al., Conversion of a B-Ketoacyl Synthase to a Malonyl Decarboxylase by Replacement of the Active-Site Cysteine with Glutamine, Biochemistry, Aug. 18, 1999, 11643-11650, 38, American Chemical Society.

Lev Kisselev, Polypeptide Release Factors in Prokaryotes and Eukaryotes: Same Function, Different Structure, Structure, Jan. 8-9, 2002, 10, Elsevier Science Ltd.

Rm Ryan; et al.; Bacterial delivery of a novel cytolysin to hypoxic areas of solid tumors, Gene Therapy, 2009, 329-339, vol. 16, Macmillan Publishers Ltd.

Dhakal, B.K., and Mulvey, M.A. (2012). The UPEC pore-forming toxin alpha-hemolysin triggers proteolysis of host proteins to disrupt cell adhesion, inflammatory, and survival pathways. Cell host & microbe 11, 58-69.

Elsen, S., Huber, P., Bouillot, S., et al. (2014). A type III secretion negative clinical strain of Pseudomonas aeruginosa employs a two-partner secreted exolysin to induce hemorrhagic pneumonia. Cell host & microbe 15, 164-176.

Gur, C., Coppenhagen-Glazer, et al. (2013). Natural killer cell-mediated host defense against uropathogenic E. coli s counteracted by bacterial hemolysinA-dependent killing of NK cells. Cell host & microbe 14, 664-674.

Huntley, U.S., Sathyamoorthy, V., et al. (1997). Membrane attack induced by HlyA, a pore-forming toxin of Vibrio cholerae. Human & experimental toxicology 16, 101-105.

Li, M., Zhang, Y., Liu, Z., et al. (2007). Aberrant expression of zinc transporter ZIP4 (SLC39A4) significantly contributes to human pancreatic cancer pathogenesis and progression. Proc Natl Acad Sci U S A 104, 18636-18641.

Liu, X., Ding, S., Shi, P., et al. (2017). Non-hemolytic enterotoxin of Bacillus cereus induces apoptosis in Vero cells. Cellular microbiology 19.

Reboud, E., Elsen, S., et al. (2016). Phenotype and toxicity of the recently discovered exlA-positive Pseudomonas aeruginosa strains collected worldwide. Environmental microbiology 18, 3425-3439.

Sastalla, I., Fattah, R., et al. (2013). The Bacillus cereus Hbl and Nhe tripartite enterotoxin components assemble sequentially on the surface of target cells and are not interchangeable. PLoS One 8, e76955.

Sathyamoorthy, V., et al. (1997). Biochemical and physiological characteristics of HlyA, a pore-forming cytolysin pf Vibrio cholerae serogroup O1. Toxicon 35, 515-527.

Sebastian Felgner, et al. (Aug. 3, 2017) Tumour-targeting bacteria-based cancer therapics for increased specificity and improved outcome Microb Biotechnol. No. 5 vol. 10 ISSN: 1751-7915.

Basso, Pauline, et al. "Pseudomonas aeruginosa pore-forming exolysin and type IV pili cooperate to induce host cell lysis." MBio 8.1 (2017): 10-1128.

* cited by examiner

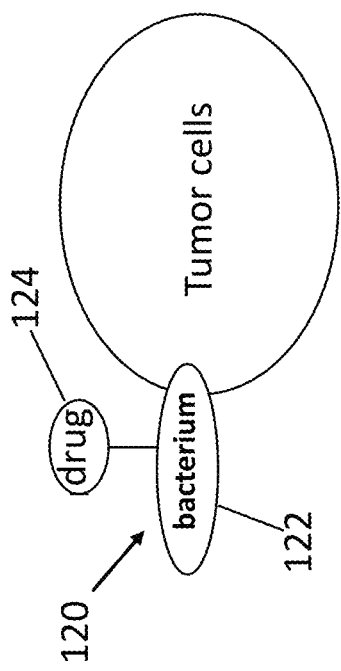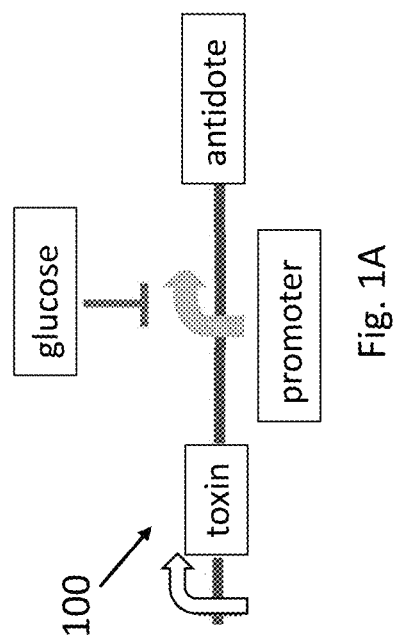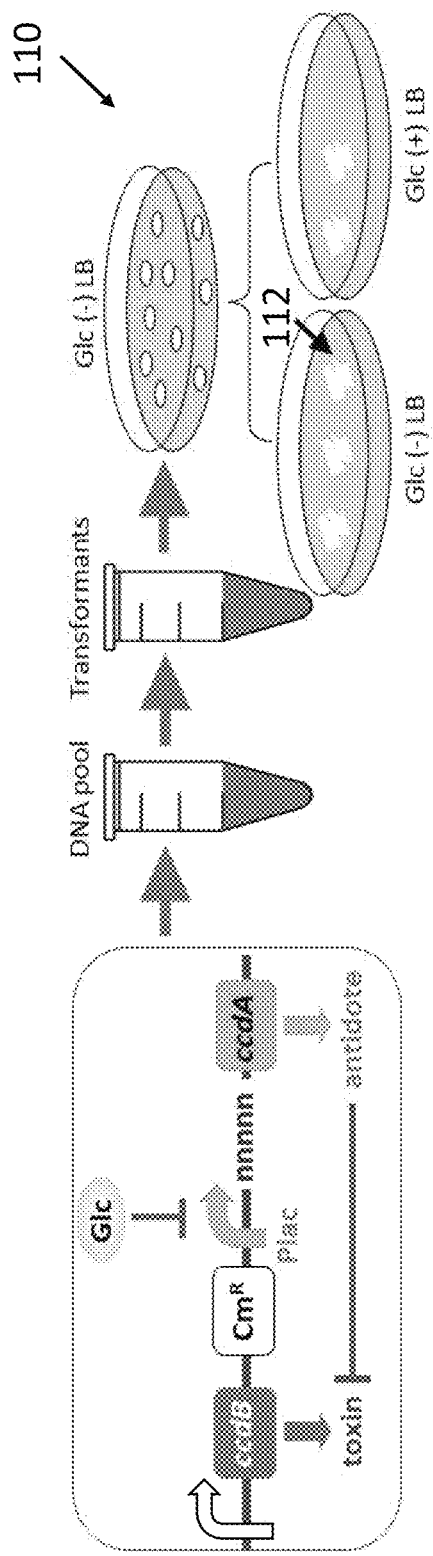
Fig. 1A
Fig. 1C
Fig. 1B liver abscess, SH1*hly* group

320

NUCLEIC ACID SYSTEMS THAT ENABLE BACTERIA TO SPECIFICALLY TARGET SOLID TUMORS VIA GLUCOSE-DEPENDENT VIABILITY

CROSS-REFERENCE TO RELATED APPLICATION

This application is a divisional application of U.S. Ser. No. 16/644,940, which is the national stage of International Application No. PCT/CN2017/101069, filed on 8 Sep. 2017, which is hereby incorporated by reference herein in its entirety

FIELD OF THE INVENTION

The present invention relates to a nucleic acid system. In particular, the present invention relates to a nucleic acid system that confers bacteria the ability to target solid tumors.

BACKGROUND

Most antitumor drugs act against all actively dividing cells, resulting in serious or even lethal side effects. Targeted therapy has to be able to discriminate tumor from non-tumor tissues when systemically administered, so that both primary and disseminated tumors are treated.

Previous targeted therapy has relied on abiotic drugs. When systemically delivered, the abiotic drugs are dramatically diluted in the bloodstream, with only a small fraction being available for tumors. Moreover, the abiotic drugs depend on tumor vasculature for delivery and thus cannot effectively diffuse to poorly vascularized and hypoxic tumor tissues. Therefore, a variety of obligate or facultative anaerobes that are capable of post-delivery reproduction and prefer poorly vascularized tumor tissues, have been evaluated for their safety and efficacy in targeting tumors over the last decades. These tumor-targeting anaerobes such as *Clostridium* and *Salmonella* could serve as carriers of tumor-killing agents and achieve targeted tumor therapy. In some cases, engineered obligate anaerobes were found to show increased tumor selectivity. Despite these progresses, the clinical use of the tumor-targeting bacteria is still far from reality because of their insufficient tumor specificity.

In view of the demand for targeted therapy with improvements for tumor specificity, tumor-targeting systems, agents and methods that destroy tumors but leave normal tissues intact are highly desired.

SUMMARY

One example embodiment is a nucleic acid system introduced into a bacterial strain to generate a genetically engineered bacterial strain. The resulting genetically engineered bacterial strain grows in solid tumors but does not grow in non-tumor tissues. The nucleic acid system includes a first DNA fragment, a second DNA fragment, a first promoter, and a first constitutive promoter. The first DNA fragment encodes a toxin gene that expresses a toxin that kills the genetically engineered bacterial strain. The second DNA fragment encodes an antidote gene that expresses an antidote that negates the toxin. The first promoter controls transcription of the antidote gene such that glucose represses the transcription of the antidote gene. The first constitutive promoter causes constitutive expression of the toxin gene. The second DNA fragment is transcribed in the solid tumors but not transcribed in the non-tumor tissues.

Other example embodiments are discussed herein.

BRIEF DESCRIPTION OF THE DRAWINGS

FIG. 1A shows a toxin-antidote genetic system that targets a bacterium to low-glucose environments in accordance with an example embodiment.

FIG. 1B shows a schematic diagram for constructing a nucleic acid system that targets *Escherichia coli* to low-glucose environments using CcdB as a toxin and CcdA as an antidote in accordance with an example embodiment.

FIG. 1C shows a drug delivery system that includes a genetically engineered bacterium that delivers anti-cancer drugs to solid tumors in accordance with an example embodiment. The anti-cancer drugs include but are not limited to anti-cancer molecules or compounds produced by the engineered bacterium or antigens that are expressed by the bacterium and able to trigger anti-cancer immune responses.

DETAILED DESCRIPTION

Figure 1D:
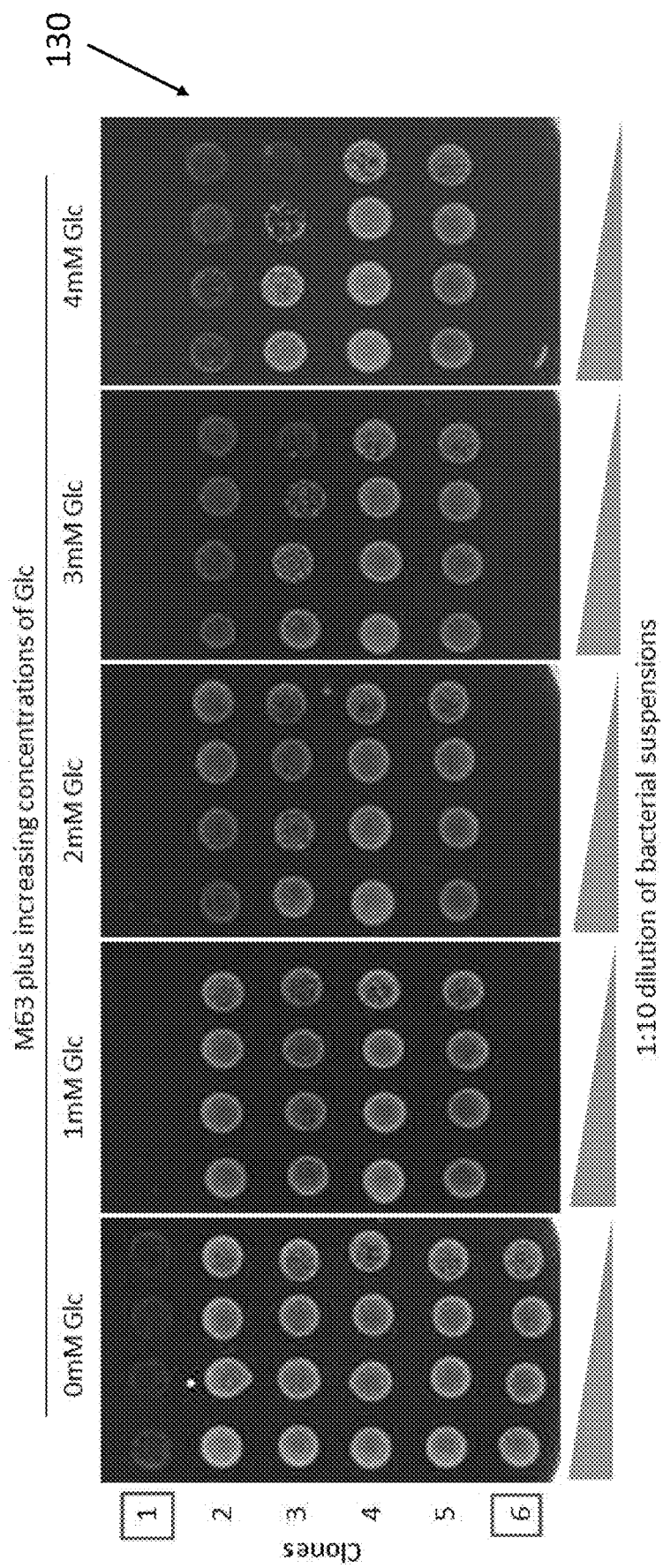
FIG. 1D shows clones that are streaked on M63 agar with different concentrations of glucose from 0 mM to 4 mM to search for those that fail to grow in the presence of glucose but glow in the absence of glucose in accordance with an example embodiment.

Example embodiments relate to a nucleic acid system. The nucleic acid system is introduced into a bacterial strain so that a genetically engineered bacterial strain targets solid tumors but leaves normal tissues intact.

Hypoxia is the most commonly utilized feature of tumor microenvironments for targeting bacteria to solid tumors. Obligate anaerobes that strictly target hypoxia, however, are confined to necrotic regions of solid tumors, whereas facultative anaerobes colonize throughout solid tumors but infect normal tissues due to its loose control of hypoxia targeting. Example embodiments in accordance with the invention solve these technical problems by introducing into bacteria a nucleic acid system that improves the tumor specificity of bacteria by regulating glucose-dependent viability of the bacteria.

FIG. 1A shows a nucleic acid system 100 including a toxin-encoding gene that is constitutively expressed, and an antidote-encoding gene under the control of a glucose-repressed promoter. The nucleic acid system confers bacteria the ability to target low-glucose environments in accordance with an example embodiment.

The toxin-antidote genetic system enables bacteria to selectively grow in glucose-deprived environments but die in the presence of glucose. As glucose deprivation is a feature of solid tumor microenvironments, the bacteria equipped with the nucleic acid system can specifically target solid tumors when applied systemically. Tumor cells are commonly deprived of glucose due to fast cell growth and excessive glucose consumption as well as inadequate blood supply. A glucose concentration is 0.123-0.424 mM in tumor tissues, and a glucose concentration is 1.22-1.29 mM in normal tissues, assuming 1 g of tissues is 1 ml. The toxin-antidote nucleic acid system enables the bacteria to selectively grow under low-glucose environments.

The nucleic acid system confers the bacteria the ability to selectively grow under low-glucose condition, which is a feature of tumor microenvironment. The bacteria such as E. coli have the intrinsic ability of preferentially growing in solid tumors and colonizing normal tissues to a lesser extent, due to the heavily immune-suppressed microenvironment of tumors. The nucleic acid system that targets low-glucose environments confers higher tumor selectivity to the bacteria such as E. coli that is not sufficiently tumor specific to be used on its own, improving safety of bacterium-mediated tumor therapy.

In an example embodiment, the nucleic acid system that is a tumor-targeting system, is integrated into the chromosome of the bacteria, such that the bacteria do not solely depend on their natural ability to target tumors and in turn the safety of the bacteria is improved. In an example embodiment, the nucleic acid system is inserted into a plasmid. In an example embodiment, the nucleic acid system is a glucose-sensing system or module.

In an example embodiment, the bacteria that carry the nucleic acid system strictly colonize solid tumors by targeting low-glucose environments.

In an example embodiment, the nucleic acid system includes a toxin-encoding gene, an antidote-encoding gene, a glucose-repressed promoter that controls the transcription of the antidote-encoding gene, and a constitutive promoter that causes constitutive expression of the toxin-encoding gene.

In an example embodiment, in environments with physiological levels of glucose, the toxin is constitutively expressed whereas the antidote expression is repressed by glucose under the control of the glucose-repressed promoter. The bacteria that carry the nucleic acid system do not grow in environments with physiological levels of glucose because the antidote is not expressed to neutralize the toxin. In low-glucose environments, both the toxin and the antidote are expressed. The bacteria that carry the nucleic acid system grow in low-glucose environments because the antidote neutralizes the toxin.

In an example embodiment, the nucleic acid system includes a toxin-encoding gene, an antidote-encoding gene, a glucose-induced promoter that controls the transcription of the toxin-encoding gene, and a constitutive promoter that causes constitutive expression of the antidote-encoding gene.

In an example embodiment, in environments with physiological levels of glucose, the antidote is constitutively expressed whereas the toxin expression is induced by glucose under the control of the glucose-induced promoter. The bacteria that carry the nucleic acid system do not grow in environments with physiological levels of glucose because the toxin is expressed to a level higher than the expression of the antidote and thereby kills the bacteria. In low-glucose environments, the toxin is not expressed so that the bacteria live and grow.

In an example embodiment, the low-glucose environments include glucose at a concentration lower than 0.424 mM. In an example embodiment, the high-glucose environments include glucose at a concentration higher than 1.22 mM. In an example embodiment, the low-glucose environments have glucose at a concentration of 0.123-0.424 mM. In an example embodiment, the high-glucose environments have glucose at a concentration of 1.22-1.29 mM.

In an example embodiment, in solid tumors, a level of the expressed antidote is higher or equivalent to that of the expressed toxin so that the toxicity of the toxin is antagonized by the antidote.

In an example embodiment, the tumor-targeting nucleic acid system is a nucleic acid system that includes a first DNA fragment that encodes a toxin gene that expresses a toxin, a second DNA fragment that encodes an antidote gene that expresses an antidote that negates the toxin, a first promoter and a first constitutive promoter. The first constitutive promoter causes constitutive expression of the toxin gene. The first promoter regulates transcription of the second DNA fragment under the control of glucose concentration, such that the second DNA fragment is transcribed under low-glucose environments or in the absence of glucose, but not transcribed in the presence of glucose or under high-glucose environments. In an example embodiment, the second DNA fragment is transcribed in the absence of glucose but not transcribed under high-glucose environments whose concentration is equal to or higher than 1 mM in M63 medium.

In an example embodiment, the first promoter controls transcription of the antidote gene, such that glucose represses the transcription of the antidote gene. The second DNA fragment is transcribed in solid tumors but not transcribed in non-tumor tissues.

In an example embodiment, the tumor-targeting nucleic acid system is a nucleic acid system that includes a first DNA fragment that encodes a toxin gene that expresses a toxin, a second DNA fragment that encodes an antidote gene that expresses an antidote that negates the toxin, a second promoter and a second constitutive promoter. The second constitutive promoter causes constitutive expression of the antidote gene. The second promoter regulates transcription of the first DNA fragment under the control of glucose concentration, such that the first DNA fragment is transcribed under high-glucose environments or in the presence of physiological levels of glucose, but not transcribed in the absence of glucose or under low-glucose environments. In an example embodiment, the first DNA fragment is not transcribed in the absence of glucose but transcribed under high-glucose environments whose concentration is equal to or higher than 1 mM in M63 medium.

In an example embodiment, the second promoter controls transcription of the toxin gene, such that glucose induces the transcription of the toxin gene. The first DNA fragment is transcribed in the non-tumor tissues but not transcribed in the solid tumors.

In an example embodiment, the first DNA fragment is shown as SEQ ID No.1. In an example embodiment, the second DNA fragment is shown as SEQ ID No.2.

In an example embodiment, the first DNA fragment is located upstream of the second DNA fragment. In an example embodiment, the first DNA fragment is located upstream of the first promoter. In an example embodiment, the first DNA fragment is located downstream of the second DNA fragment. In an example embodiment, the second promoter is located upstream of the first DNA fragment. In an example embodiment, the first constitutive promoter is located upstream of the first DNA fragment. In an example embodiment, the second constitutive promoter is located upstream of the second DNA fragment. In an example embodiment, the first promoter is shown as SEQ ID No.3.

In an example embodiment, the nucleic acid system includes a random sequence that consists of 5-6 nucleotides, and is located immediately upstream of the second DNA fragment and downstream of the first promoter. In an example embodiment, the random sequence is GCCTT or TGTCT.

In an example embodiment, the nucleic acid system includes a random sequence that consists of 5-6 nucleotides, and is located immediately upstream of the first DNA fragment and downstream of the second promoter.

In an example embodiment, the nucleic acid system includes a random sequence that consists of 5-6 nucleotides, and replaces original or native 5-6 nucleotides of the bacteria that are located immediately upstream of the second DNA fragment.

In an example embodiment, the nucleic acid system includes a random sequence that consists of 5-6 nucleotides, and replaces original or native 5-6 nucleotides of the bacteria that are located immediately upstream of the first DNA fragment.

In an example embodiment, the nucleic acid system includes a random sequence that consists of 5-6 nucleotides, and replaces original or native 5-6 nucleotides of the first promoter. In an example embodiment, the nucleic acid system includes a random sequence that consists of 5-6 nucleotides, and replaces original or native 5-6 nucleotides of the second promoter.

In an example embodiment, the random sequence is located downstream of the first promoter. In an example embodiment, the random sequence is located immediately upstream of the second DNA fragment.

In an example embodiment, the random sequence is located downstream of the second promoter. In an example embodiment, the random sequence is located immediately upstream of the first DNA fragment.

In an example embodiment, the nucleic acid system includes a third DNA fragment that encodes a selectable marker. In an example embodiment, the marker is chloramphenicol selectable marker ($Cm^R$). In an example embodiment, the selectable marker is a chloramphenicol resistance cassette. In an example embodiment, the third DNA fragment is shown as SEQ ID No. 4.

In an example embodiment, the third DNA fragment is located downstream of the first DNA fragment and upstream of the first promoter. In an example embodiment, the third fragment is located downstream of the second DNA fragment and upstream of the second promoter.

In an example embodiment, the nucleic acid system includes SEQ ID No.1, SEQ ID No.2, SEQ ID No.3, and SEQ ID No.4. In an example embodiment, the nucleic acid system includes a constitutive promoter to drive expression of ccdB as shown in SEQ ID No. 5. In an example embodiment, the nucleic acid system includes a rrnB transcription termination region as shown in SEQ ID No. 6. In an example embodiment, the nucleic acid system is shown as SEQ ID No. 7. In an example embodiment, the nucleic acid system is shown as SEQ ID No. 8.

In an example embodiment, the nucleic acid system includes a toxin gene, an antidote gene, a first promoter that controls transcription of the antidote gene, and a constitutive promoter for the toxin gene. In an example embodiment, the nucleic acid system includes a toxin gene, an antidote gene, a second promoter that controls transcription of the toxin gene, and a constitutive promoter for the antidote gene.

In an example embodiment, the bacterial strain is a Gram-positive bacterial strain. In an example embodiment, the bacterial strain is a Gram-negative bacterial strain.

In an example embodiment, the bacterial strain is *Escherichia coli*. In an example embodiment, the bacterial strain is selected from a group consisting of *Escherichia coli* MG1655 and *Escherichia coli* SH1.

FIG. 1B shows a schematic diagram 110 for constructing a nucleic acid system that targets *E. coli* to low-glucose environments in accordance with an example embodiment. FIG. 1B shows that a randomized, glucose-repressed lactose promoter (Plac) and a CcdA/CcdB toxin-antidote pair are employed to construct a nucleic acid system that targets *E. coli* to low-glucose environments.

CcdB is a toxin that kills host bacteria, and CcdA is an antidote to counteract CcdB. In the tumor-targeting nucleic acid system, CcdB is constitutively expressed whereas CcdA expression is repressed by glucose under the control of the glucose-repressed lactose (lac) promoter. In low-glucose environments, bacteria carrying this nucleic acid system shall grow well because the antidote CcdA is de-repressed to neutralize CcdB. In the presence of physiological levels of glucose, CcdA expression is turned off and CcdB is freed up to kill the bacteria.

In an example embodiment, in the tumor-targeting nucleic acid system, CcdA is constitutively expressed whereas CcdB expression is induced by glucose under the control of the glucose-induced promoter. In low-glucose environments, bacteria carrying this nucleic acid system shall grow well because the toxin CcdB is repressed. In the presence of physiological levels of glucose, CcdB expression is turned on to kill the bacteria.

As shown in FIG. 1B, a randomized fragment composed of 5-6 nucleotides (nnnnn) replaces the original or native 5-6 nucleotides immediately upstream of the start codon of the ccdA gene (one example of the second DNA fragment). Different sequences in this randomized fragment result in different levels of the ccdA expression. With some sequences, the glucose levels in tumors are low enough to activate the expression of CcdA to antagonize the toxicity of CcdB, and the glucose levels in normal tissues are high enough to shut down the CcdA expression under the control of the lac promoter. A selectable marker, such as chloramphenicol selectable marker ($Cm^R$) is also used in the nucleic acid system of FIG. 1B.

The nucleic acids systems with different sequences in the randomized fragment (a random library of the nucleic acid systems or DNA pool) are inserted into the chromosome of *E. coli* and the bacteria are then streaked on lysogeny broth (LB) agar plates with glucose (Glc (+)) or without glucose (Glu (−)) to screen those that fail to grow in the presence of glucose but grow in the absence of glucose. The arrow 112 indicates a clone that grows in glucose-negative medium but does not grow in medium with glucose. In an example embodiment, the concentrations of glucose on LB agar plates are 0 mM or 5 mM.

FIG. 10 shows a drug delivery system 120 that includes a genetically engineered bacterium 122 that not only specifically targets solid tumors but also delivers to solid tumors anti-cancer drugs 124 by producing anti-cancer molecules or compounds and/or expressing antigens that trigger anti-cancer immune responses.

The genetically engineered bacterium 122 delivers the drug 124 to solid tumors and kills the tumor cells. The genetically engineered bacterium 122 includes the nucleic acid system discussed herein, such that the bacterium grows in the solid tumors but not grow in non-tumor tissues.

The following examples are provided illustrating various embodiments.

EXAMPLE 1

Materials and Methods

Construction of a random library of engineered *E. coli* that targets low-glucose environments:

The tumor-targeting nucleic acid system designed in this example was composed of a constitutively expressed ccdB gene and a glucose-repressed ccdA gene under the control of a lac promoter. The antidote CcdA is repressed in the presence of physiological levels of glucose so that the toxin CcdB kills the bacteria. In contrast, the bacteria are alive under the low-glucose growth conditions because the expression of CcdA is de-repressed and counteracts the action of CcdB. To improve the capacity of CcdA in antagonizing CcdB under the control of the lac promoter under the low-glucose conditions or enhancing the ability of CcdB to kill bacteria in the presence of glucose, a random library of the tumor-targeting nucleic acid system was constructed by randomizing the 5 nucleotides immediately upstream of the start codon of the ccdA gene. To facilitate the genetic engineering on the chromosome by the λ-Red recombination technique, a selectable marker, chloramphenicol selectable marker ($Cm^R$), was included in the tumor-targeting nucleic acid system as illustrated in FIG. 1B.

Specifically, a set of DNA fragments (i.e. tumor-targeting nucleic acid systems) that contains the ccdB gene under the control of a constitutive promoter, a selectable marker (such as the loxP-cat-loxP cassette), a 5 nucleotides (5 nt)-randomized region, and the ccdA gene under the control of a glucose-repressed promoter (such as a lac promoter) was generated by overlapping polymerase chain reaction (PCR) as shown in FIG. 1B. The 5 nt-randomized region allows for generating a random library of the nucleic acid systems. The selectable marker makes it possible to insert the nucleic acid systems into the chromosome of bacteria by recombineering. Then, the library of the nucleic acid systems was inserted into the chromosome of *E. coli*, using the λ-Red recombineering technique. After 1 h-recovery in glucose-deprived LB, the bacterial culture was spread on glucose-deprived LB agar supplemented with antibiotics (12.5 µg/ml chloramphenicol if the loxP-cat-loxP cassette was used as the selectable marker). After overnight culture at 32° C., individual colonies formed on the agar. Each colony is derived from replication of a single *E. coli* that has the potential to selectively grow under low-glucose conditions. These colonies formed a random library of putative tumor-targeting bacteria. Here, the CcdB-CcdA pair could be replaced by other toxin-antidote pair.

Library screen for bacteria targeting glucose-deprived environment: Glucose-deprived LB medium was used for library screen for bacteria that selectively grew under low-glucose conditions. To screen the random library, each of the clones was streaked both on the glucose-deprived LB agar and LB agar plus 5 mM glucose. After overnight culture at 37° C., clones that were found to grow readily on the glucose-deprived LB agar but not to grow on glucose-positive LB agar were further assessed using the minimal M63 medium agar. The M63 agar was supplemented with increasing concentrations of glucose in addition to 30 mM glycerol. Here, bacteria strains other than *E. coli* MG1655 could be used for screening for tumor-targeting bacteria using the same strategy.

In vivo assessment of the tumor-targeting efficacy of engineered bacteria: Six- to eight-week-old nude mice were used for tumor implantation of human cancer cell lines, and six- to eight-week-old immunocompetent BALB/c mice were used for tumor implantation of murine derived cell lines. $1 \times 10^7$ of bacteria were injected into the tail vein of each mouse. Tumor size was measured using digital calipers every three days following the bacterial injection. At the end of the experiments, mice were euthanized and their tumors and organs were removed for determination of colony forming unit. Specifically, 1 gram of tissues was homogenized in 1 ml of Phosphate-buffered saline (PBS) buffer. The resulting tissue suspensions were serially diluted and plated, and colony forming units of the diluted suspensions were counted. The number of bacteria in each tissue was calculated according to dilution ratio. Bacteria were regarded as being able to specifically target tumors if they were present in tumors but absent from organs.

In an example embodiment, the tumor-targeting nucleic acid system is composed of the constitutively expressed ccdB gene, a $Cm^R$ cassette and lac promoter-controlled ccdA with a 5 nt-random sequence being located immediately upstream its start codon. These elements are not necessarily placed in the order as shown in FIG. 1B. In an example embodiment, the tumor-targeting nucleic acid system is composed of the constitutively expressed ccdA gene, a $Cm^R$ cassette and a glucose-induced promoter-controlled ccdB with a 5 nt-random sequence being located immediately upstream its start codon. The ccdB-ccdA pair can be replaced by other toxin-antitoxin pair. $Cm^R$ can be replaced by other selectable markers. The number of nucleotides in the random sequence is not confined to five.

EXAMPLE 2

*E. coli* MG1655 was used in this example. The constitutively expressed CcdB, the lac promoter-controlled CcdA, the lac promoter, and $Cm^R$ were used to construct the tumor-targeting nucleic acid system. The ccdB gene was located upstream of the $Cm^R$ cassette that was located upstream of the lac promoter. A random library of the putative tumor-targeting bacteria was generated by inserting a randomized fragment (5 nucleotides in this example) in the lac promoter immediately upstream of the ccdA gene. The random library was chromosomally established in the *E. coli* strain MG1655. In this random library, each *E. coli* MG1655 variant carried in the chromosome a lac promoter variant with a distinctive 5 nucleotide-sequence in the randomized domain. The random library was screened to search for bacterial clones that selectively grew under low-glucose conditions. Specifically, the library was established on LB agar depleted for glucose. The resulting *E. coli* clones were then individually streaked on both LB agar with 5 mM glucose and LB agar without glucose to screen for those that failed to grow in the presence of glucose but grew in the absence of glucose. Approximately 1500 clones were screened and 6 clones were found to preferentially grow in glucose-negative medium.

FIG. 1D shows drawings 130 for the sensitivity of six *E. coli* clones to glucose on minimal medium M63 agar. The 6 clones were purified, incubated overnight, and serially diluted. 10 μl of each diluted suspension was dropped on minimal medium M63 supplemented with increasing concentrations of glucose (Glu) from 0 mM Glu to 4 mM Glu to verify their phenotype. Among the 6 clones, the $1^{st}$ and the $6^{th}$ clones grew well on glucose-negative medium agar, but grew poorly in the presence of glucose. In the contrast, the $2^{nd}$, $3^{rd}$, $4^{th}$ and $5^{th}$ clones displayed considerable growth in both glucose-negative and glucose-positive medium agar. Given this, the $1^{st}$ and the $6^{th}$ clones (boxed in FIG. 1D) were candidates of tumor-targeting bacteria and named JY1 and JY6 (also named JY8), respectively. If more library screening was carried out, more glucose-sensing clones could be identified.

The random sequence upstream of the ccdA gene in the chromosome of the clone JY1 is GCCTT. The nucleotide sequence of JY1 includes a sequence as shown in SEQ No. 5. The random sequence upstream of the ccdA gene in the chromosome of the clone JY6 is TGTCT.

The strain JY1 was deposited at the China General Microbiological Culture Collection Center (CGMCC) under deposit no. 14577. The strain JY6 was deposited at the CGMCC under deposit no. 14578.

EXAMPLE 3

The engineered *E. coli* variants JY1 and JY6 were sensitive to glucose and failed to grow in the presence of glucose in vitro. This example provides in vivo experiments and data showing that glucose levels in tumors were low enough for JY1 and JY6 to survive and grow. JY1 and JY6 were separately injected into the tail vein of immunocompetent BALB/c mice with CT26 (a murine colorectal cancer cell line) tumors ($10^7$ cfu/mouse). The parental strain MG1655 was employed as a control. 15 days after the tail vein injection, the bacteria were analyzed for their distribution in tumor and liver. The liver was chosen for the analyses because it is more vulnerable to bacterial infection than other organs.

FIGS. 2A-2F show *E. coli* JY1 and JY6 specifically targeted tumors in mice. Error bar, SEM. *$P<0.05$, **$P<0.01$.

Figures 2A, 2B:
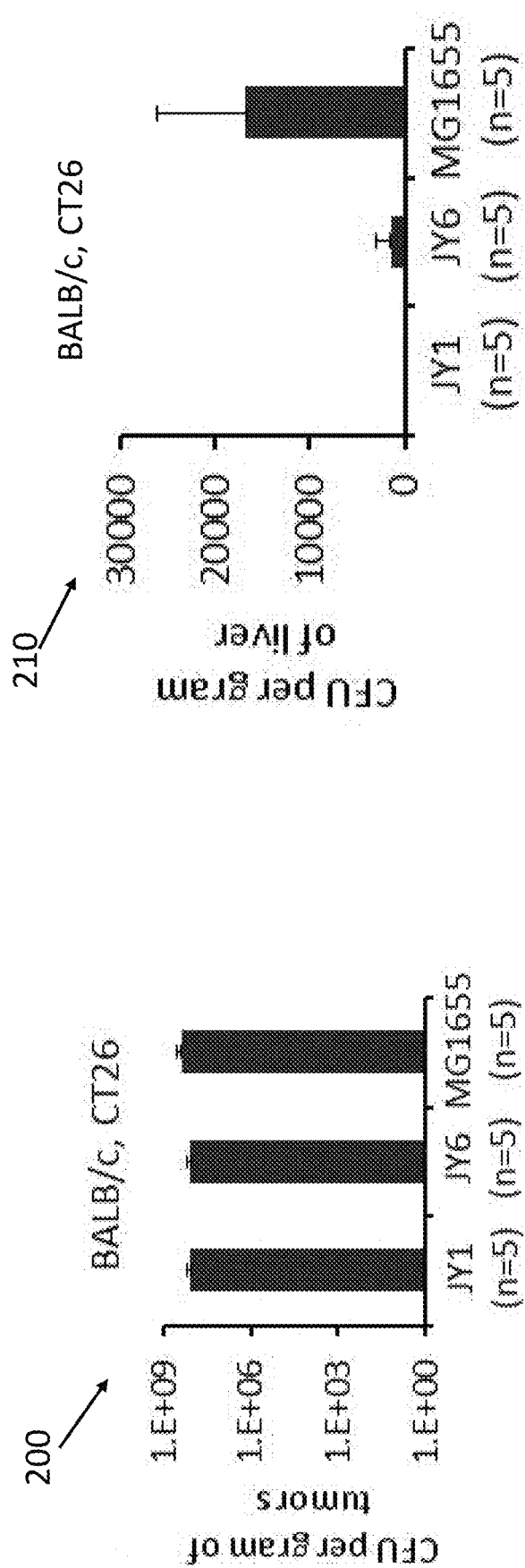
FIG. 2A shows colonization of the genetically engineered bacterial strains JY1 and JY6, and an unmodified wild-type *E. coli* strain named MG1655 in CT26 (a murine colorectal cancer cell line) tumors of Bagg albino/c (BALB/c) mice 15 days after intravenous injection of the bacteria ($10^7$/mouse) in accordance with an example embodiment.
FIG. 2B shows colonization of the bacterial strains JY1, JY6, and MG1655 in the liver of BALB/c mice with CT26 tumors 15 days after intravenous injection of the bacteria ($10^7$/mouse) in accordance with an example embodiment.

FIG. 2A shows colony forming unit (CFU) 200 per gram of CT26 tumors in BALB/c mice. As shown in FIG. 2A, JY1, JY6, and MG1655 comparably colonized the CT26 tumors in the BALB/c mice and their levels in the tumors were over $10^8$ cfu/g. These data showed that both JY1 and JY6 were good colonizers in the CT26 tumors carried by the immunocompetent BALB/c mice.

Figures 2C, 2D:
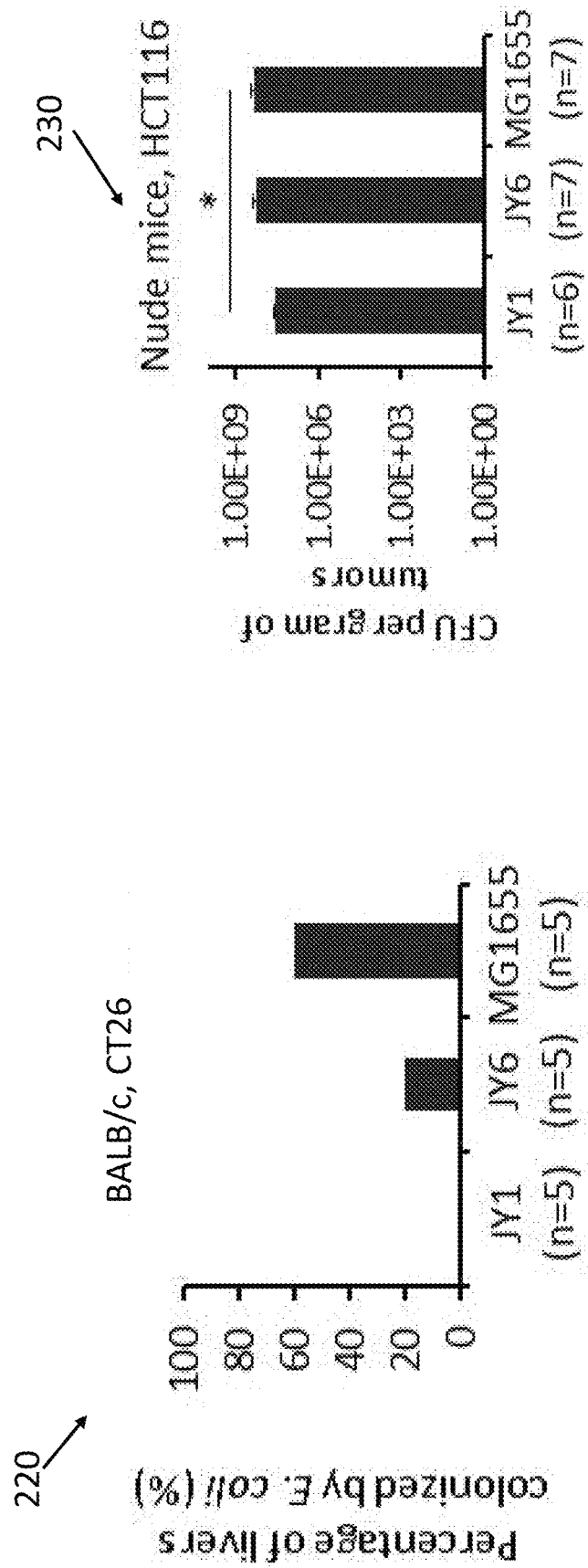
FIG. 2C shows percentage of livers colonized by the bacterial strains JY1, JY6, and MG1655 in BALB/c mice with CT26 tumors 15 days after intravenous injection of the bacteria ($10^7$/mouse) in accordance with an example embodiment.
FIG. 2D shows colonization of the bacterial strains JY1, JY6, and MG1655 in tumors in nude mice with HCT116 (a human colorectal cancer cell line) tumors 7 days after intravenous injection of the bacteria ($10^7$/mouse) in accordance with an example embodiment.

FIG. 2B shows CFU 210 per gram of liver in BALB/c mice with CT26 tumors. As shown in FIG. 2B, JY1 did not colonize the liver of BALB/c mice with CT26 tumors. JY6 colonized the liver of BALB/c mice with CT26 to a less extent than MG1655 did. FIG. 2C shows percentages 220 of livers colonized by JY1, JY6 and MG1655 in BALB/c mice with CT26 tumors. As shown in FIG. 2C, JY6 was detected in the livers of 20% of the BALB/c mice with CT26 tumors (1 out of 5) and JY1 was not detected in the liver of any mouse, while MG1655 colonization occurred in the livers of 60% of the mice (3 out of 5). These showed that JY1 and JY6 are more specific to tumors than MG1655 and that JY1 is more specific to tumors than JY6.

Further plating analyses showed that JY1 was also absent from blood and organs including spleen, heart, lung and kidney of the immunocompetent mice. Although JY1 and JY6 displayed comparable ability to colonize the CT26 tumors, JY1 was superior in specifically targeting the tumors than JY6 in the immunocompetent mice.

Figure 2F:
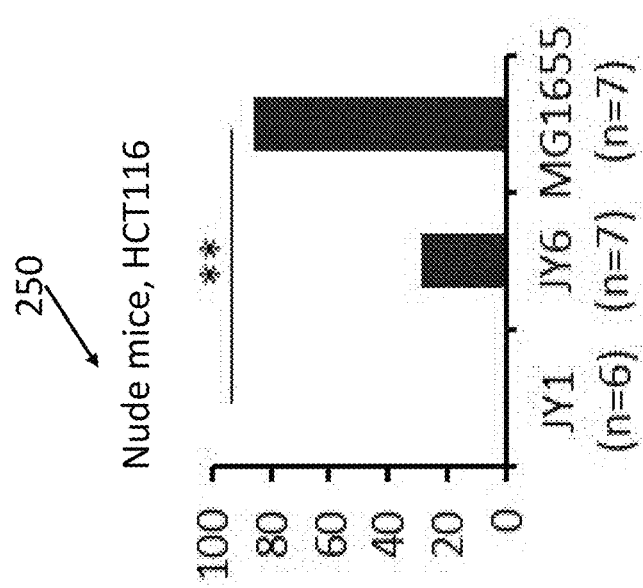
FIG. 2F shows percentage of livers colonized by the bacterial strains JY1, JY6, and MG1655 in nude mice with HCT116 tumors 7 days after intravenous injection of the bacteria ($10^7$/mouse) in accordance with an example embodiment.
Figure 2E:
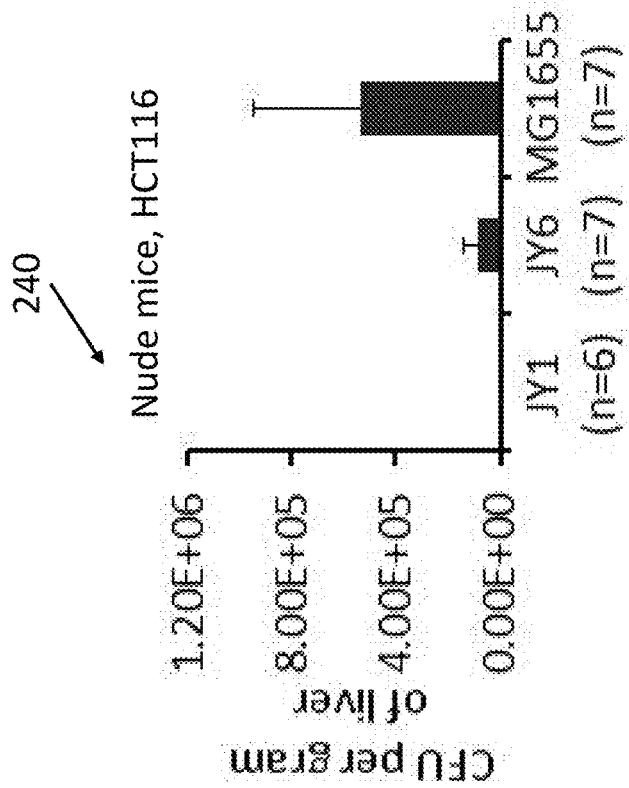
FIG. 2E shows colonization of the bacterial strains JY1, JY6, and MG1655 in the liver of nude mice with HCT116 tumors 7 days after intravenous injection of the bacteria ($10^7$/mouse) in accordance with an example embodiment.

Similar experiments were performed in immunocompromised nude mice carrying subcutaneous HCT116 (a human colorectal cancer cell line) tumors. 7 days after the tail vein injection of the bacteria ($10^7$ cfu/mouse), the bacteria were analyzed in their distribution in tumor and liver. FIG. 2D shows CFU 230 per gram of the HCT116 tumors in nude mice. As shown in FIG. 2D, JY1, JY6, and MG1655 colonized the HCT116 tumors in the nude mice. FIG. 2E shows CFU 240 per gram of liver in nude mice with HCT116 tumors. As shown in FIG. 2E, JY1 did not colonize the liver of nude mice with HCT116 tumors. JY6 colonized the liver of nude mice with HCT116 tumors to a less extent than MG1655 did. FIG. 2F shows percentage 250 of livers colonized by JY1, JY6 and MG1655 in nude mice with HCT116. As shown in FIG. 2F, JY6 and MG1655 were detected in the livers of 28.57% (2 out of 7) and 85.71% (6 out of 7) of the nude mice, respectively. Again, JY1 was not present in the liver of any mouse (n=6). These showed that JY1 and JY6 are more specific to tumors in immunocompromised mice than MG1655 and that JY1 is more specific to tumors than JY6 in immunocompromised mice.

To ensure that JY1 did not infect normal tissues, blood and homogenized suspensions of the spleen, heart, lung and kidney of each mouse in the bacteria-treated group were further examined. All these were cleared of JY1. Although JY1 avoided infecting organs, it readily colonized the HCT116 tumors and its levels in the tumors reached $3.79 \times 10^7$ cfu/g (FIG. 2D). Taken together, the in vivo data demonstrate that the tumor-targeting nucleic acid system carried by the bacteria JY1 and JY6 enables them to specifically target solid tumors in both immunocompetent and immunocompromised mice, and JY1 was superior to JY6 in the ability of targeting solid tumors.

EXAMPLE 4

The glucose-targeting nucleic acid system carried by JY1 was next grafted into the chromosome of *E. coli* SH1, to show that this nucleic acid system is not confined to a particular bacterial strain.

*E. coli* SH1 was isolated from a stool sample provided by a healthy female volunteer. The stool sample was resuspended in PBS buffer and spread on LB agar supplemented with 1 mM isopropyl β-D-thiogalactoside (IPTG) and X-gal (0.06 mg/ml). *E. coli* formed blue colonies and were discriminated from other bacteria species. SH1 is one of the fecal *E. coli* isolates. The strain SH1 was deposited at the CGMCC under deposit no. 14580.

The resulting recombinant *E. coli* strain was referred to as JYH1. The strain JYH1 was deposited at the CGMCC with deposit no. 14579.

JYH1 was then intravenously injected into nude mice carrying subcutaneous SW480 (a human colorectal cancer cell line) tumors. The mice were analyzed for bacterial colonization in tumors and organs 90 days after the intravenous injection of the bacteria. Because the tumors of four JYH1-treated mice were completely cured, only two tumors in this group were available for analysis. JYH1 was detected from one of the two tumors, reaching $1.8 \times 10^8$ cfu per gram.

It shows that when the module or the nucleotide system is introduced into *E. coli* SH1, the resulting strains can not only target tumors but also treat tumors.

Figure 3B:
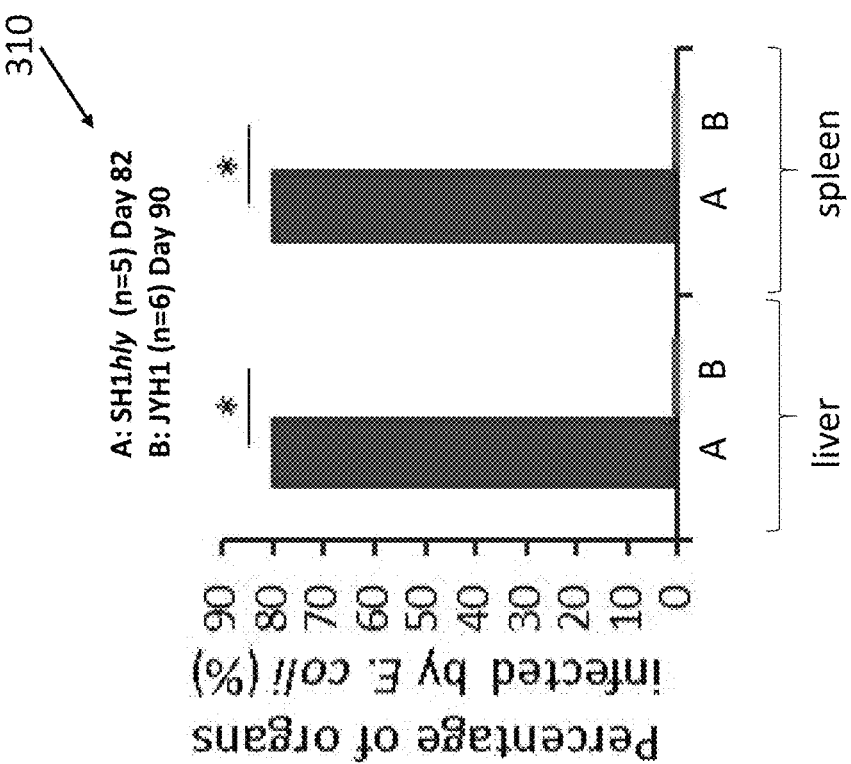
FIG. 3B shows percentages of liver and spleen infected by the bacterial strains JYH1 and SH1 hly in nude mice carrying subcutaneous SW480 tumors in accordance with an example embodiment.
Figure 3A:
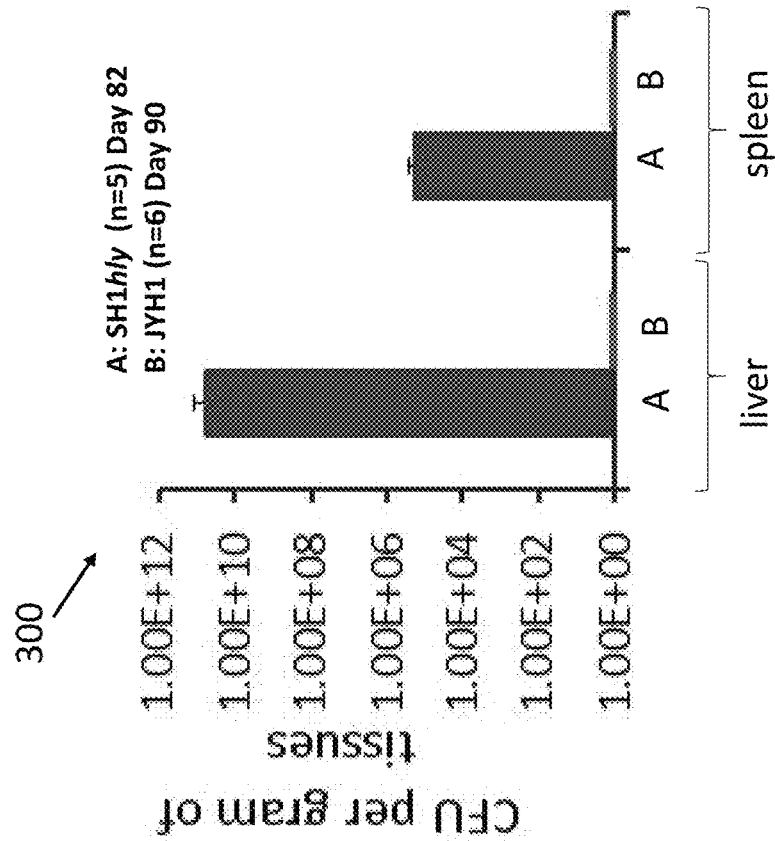
FIG. 3A shows colonization of the bacterial strains JYH1 and SH1 hly in liver and spleen of nude mice carrying subcutaneous SW480 (a human colorectal cancer cell line) tumors in accordance with an example embodiment.

FIGS. 3A and 3B show *E. coli* JYH1 specifically targeted SW480 tumors and did not colonize normal tissues in nude mice, while its isogenic strain SH1 hly that was not engineered by the tumor-targeting nucleotide system colonized both tumors and normal tissues. *$P<0.05$. Error bar, SEM.

FIG. 3A shows CFU 300 per gram of liver and spleen tissues in nude mice with SW480. FIG. 3B shows percentage 310 of liver and spleen organs infected by JYH1 and SH1 hly. As shown in FIGS. 3A and 3B, JYH1 did not colonized liver or spleen. The livers, spleens, hearts, lungs, kidneys of all the JYH1-treated nude mice were all cleared of JYH1, indicating that the glucose-sensing module is able to confine JYH1 to tumors and prevent it from spreading to distant organs for a long time. In contrast to JYH1, its isogenic strain SH1 hly that is not equipped with the glucose-sensing module colonized not only tumors ($9.35 \times 10^8 \pm 5.97 \times 10^8$ cfu/g, mean±SEM) but also organs. The livers ($6.0 \times 10^{10} \pm 6.0 \times 10^{10}$ cfu/g, mean±SEM) and spleens ($1.85 \times 10^5 \pm 9.74 \times 10^4$ cfu/g, mean±SEM) of four SH1 hly-treated mice (80%, 4 out of 5) were infected by SH1 hly when analyzed on day 82.

Figure 3C:
FIG. 3C shows liver abscess developed in a mouse treated with the bacterial strain SH1 hly in accordance with an example embodiment.

Among the infected mice, one mouse developed liver abscess as shown in FIG. 3C. The picture 320 was taken on day 82 when the mouse was euthanized for analysis.

Figure 3D:
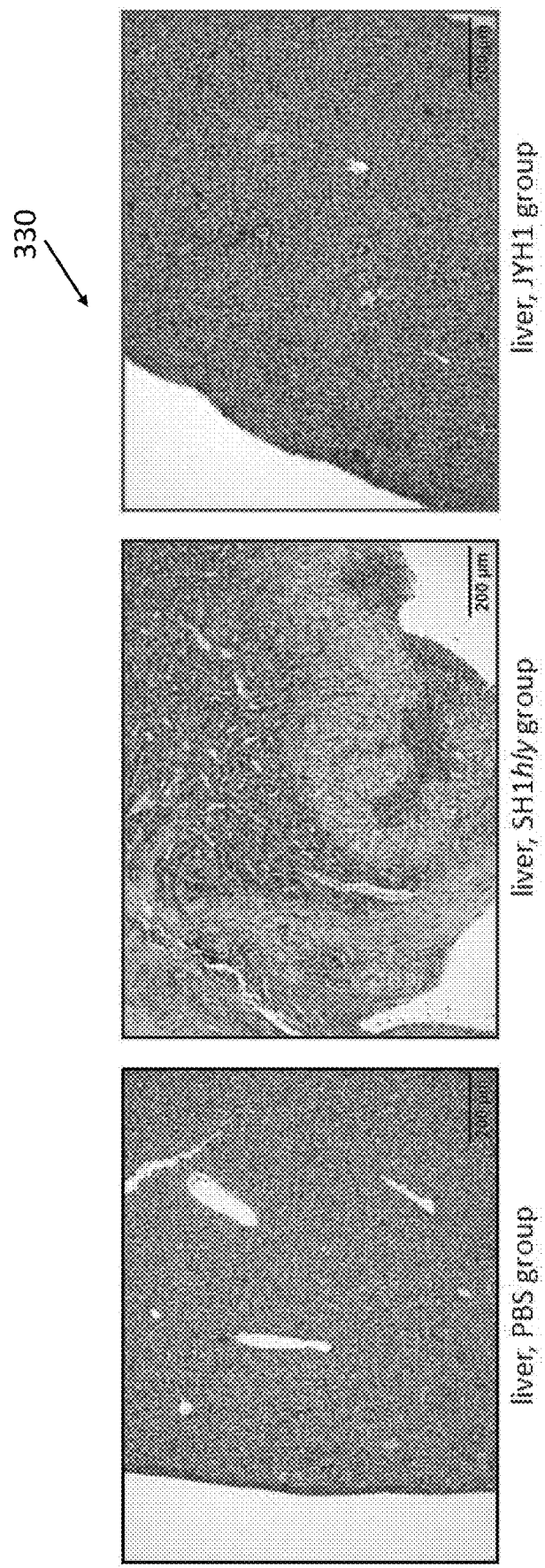
FIG. 3D shows microscopic images of Hematoxylin and Eosin (H&E)-stained liver sections from nude mice carrying subcutaneous SW480 tumors that are treated with Phosphate-buffered saline (PBS), strains SH1 hly and JYH1 in an accordance with an example embodiment.

Tumor specificity of JYH1 and its requirement of the glucose-sensing, tumor-targeting nucleic acid system were also confirmed by Hematoxylin and Eosin (H&E) staining of liver sections 330, which showed that the liver of JYH1-treated mice was normal whereas massive inflammatory infiltration and abscess occurred in the liver of SH1 hly-treated mice as shown in FIG. 3D (Scale bar, 200 μm). Taken together, these data demonstrate that the glucose-sensing tumor-targeting nucleic acid system optimizes tumor specificity of JYH1 in nude mice.

EXAMPLE 5

Figure 4:
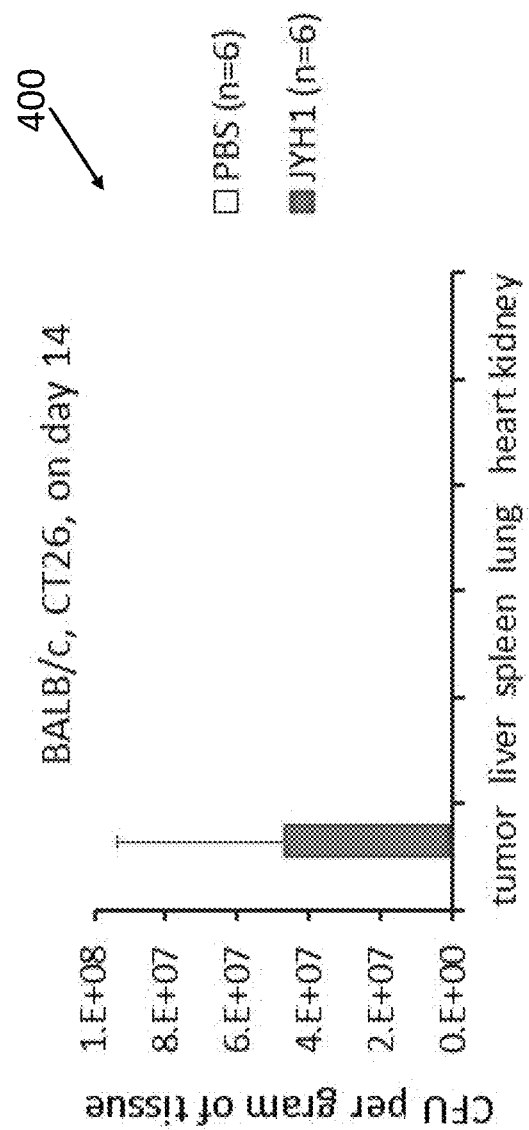
FIG. 4 shows the targeting efficacy of intravenously injected strains JYH1 on CT26 tumors of immunocompetent BALB/c mice in accordance with an example embodiment.

The ability of JYH1 in specifically colonizing tumors in immunocompetent mice was tested. JYH1 was intravenously administered to immunocompetent BALB/c mice carrying CT26 tumors. 14 days after the bacterial injection, all the mice were euthanized due to excessive tumor growth. FIG. 4 shows CFU 400 per gram of normal tissues and CT26 tumors in BALB/c mice. Plating analysis of homogenized tissues showed that the intravenously injected JYH1 did not colonize any organs tested including the liver, spleen, heart, lung and kidney of the immunocompetent mice on day 14. In contrast, levels of JYH1 in the tumors reached $4.67 \times 10^7$ cfu per gram ($\pm 1.62 \times 10^7$ cfu/g) as shown in FIG. 4. These together with the data from the nude mice demonstrate that JYH1 specifically targets solid tumors regardless of the integrity of the immune system.

Figure 5:
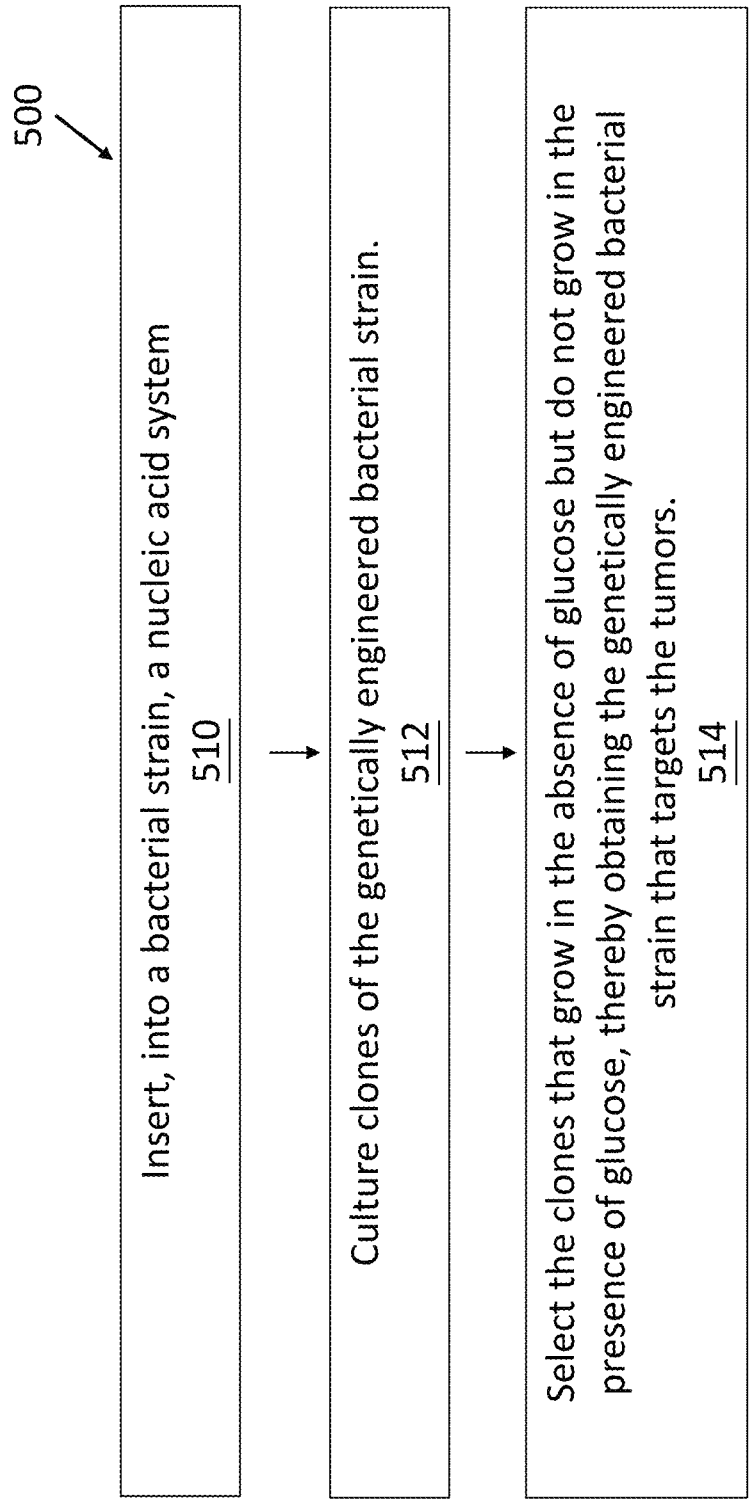
FIG. 5 show a method to construct a genetically engineered bacterial strain that targets solid tumors by selectively living and growing in glucose-deprived regions in accordance with an example embodiment.

FIG. 5 shows a method 500 of constructing a genetically engineered bacterial strain that targets solid tumors by selectively growing in glucose-deprived environments.

Block 510 states inserting into a bacterial strain a nucleic acid system.

In an example embodiment, the nucleic acid system includes a first DNA fragment that encodes a toxin, a second DNA fragment that encodes an antidote that negates the toxin. The nuclei acid system also includes a first promoter that controls transcription of the second DNA fragment. The nucleic acid system also includes a first constitutive promoter that causes constitutive expression of the first DNA fragment.

In an example embodiment, the nucleic acid system includes a first DNA fragment that encodes a toxin, a second DNA fragment that encodes an antidote that negates the toxin. The nuclei acid system also includes a second promoter that controls transcription of the first DNA fragment. The nucleic acid system also includes a second constitutive promoter that causes constitutive expression of the second DNA fragment.

In an example embodiment, the toxin-antidote pair includes but is not limited to the CcdB-CcdA pair. Other toxin-antidote pairs such as AvrRxo1-Arc1, Hha-TomB, and PaaA2-ParE2 can be used to replace the CcdB-CcdA pair. In an example embodiment, the first promoter includes but is not limited to the lac promoter. The lac promoter can be replaced by other glucose-repressed promoters such as the promoters of gltA, sdhADC or tnaB. In an example embodiment, the second promoter includes but is not limited to the promoter of ptsG, the promoter of fruB and the promoter of ackA.

In an example embodiment, a random sequence that consists of 5-6 nucleotides is inserted to replace the native 5-6 nucleotides immediately upstream of the start codon of the ccdA gene and downstream of the first promoter.

In an example embodiment, a random sequence that consists of 5-6 nucleotides is inserted to replace the native 5-6 nucleotides immediately upstream of the start codon of the ccdB gene and downstream of the second promoter.

Block 512 states culturing the clones of the genetically engineered bacterial strain.

In an example embodiment, the nucleic acid system is grafted into the chromosome of the bacterial strain. In an example embodiment, the nucleic acid system is grafted into a plasmid and the plasmid is inserted into the bacterial strain. In an example embodiment, the bacterial strain includes but is not limited to *Escherichia coli* MG1655. Other *Escherichia coli* strains such as DH5α and CFT073 and other Gram-negative bacterial species such as *Salmonella* and *Shigella* may be used to replace MG1655. In an example embodiment, clones of the bacterial strain that includes the nucleic acid system are cultured on LB agar with or without glucose.

Block 514 states selecting the clones that grow in the absence of glucose but do not grow in the presence of glucose, thereby obtaining the genetically engineered bacteria strain that targets the tumors.

In an example embodiment, the clones that grow in LB agar without glucose but do not grow in LB agar with 5 mM glucose are selected and identified as potential candidates of tumor-targeting bacteria.

In an example embodiment, the clones that grow in M63 agar without glucose but do not grow at glucose concentrations of 1-4 mM are confirmed as potential candidates of tumor-targeting bacteria.

In an example embodiment, the method further includes generating a random library of the nucleic acid system by inserting a random sequence that consists of 5-6 nucleotides to replace native nucleotides that are located immediately upstream of the second DNA fragment, when the nucleic acid system includes the first promoter.

In an example embodiment, the method further includes generating a random library of the nucleic acid system by inserting a random sequence that consists of 5-6 nucleotides to replace native nucleotides that are located immediately upstream of the first DNA fragment, when the nucleic acid system includes the second promoter.

EXAMPLE 6

This example shows that *E. coli* SH1 is cytotoxic to cancer cell lines. SW480 and HCT116 are colorectal cancer cell lines. ASPC-1, Mia-capa-2, and panc-1 are pancreatic cancer cell lines. Each of the cell lines was co-cultured with *E. coli* strain SH1 or MG1655 at a moi of 100. As controls, the cells lines were also co-cultured with PBS alone. After 4 hours, the cells were washed with PBS and stained with 1% crystal violet for 5 min. The stained cells were washed again, destained with 95% ethanol, and measured at 570 nm. Percentage of cells killed by the co-cultured bacteria was calculated using the formula: (control−treat)/control×100. Error bar, SEM. ***$P<0.001$.

Figures 6A, 6B:
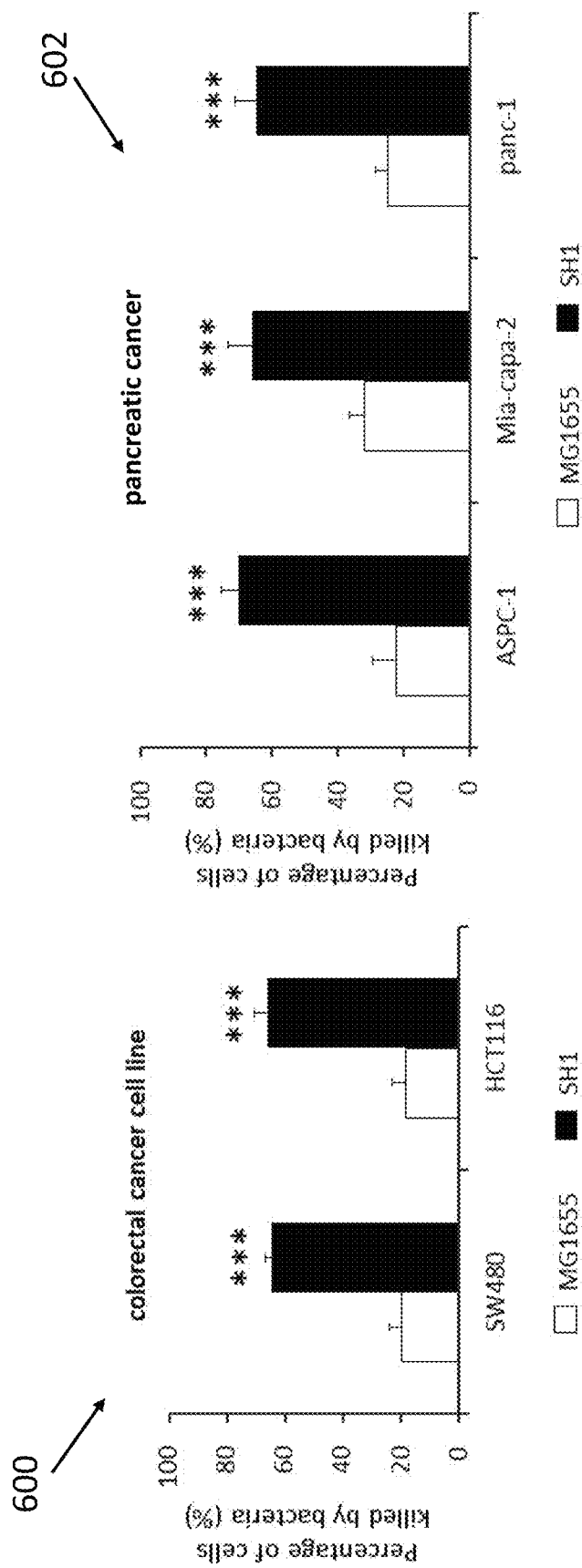
FIG. 6A shows the in vitro cytotoxic effect of E. coli SH1 and E. coli MG1655 on SW480 and HCT116 cells in accordance with an example embodiment.
FIG. 6B shows the in vitro cytotoxic effect of E. coli SH1 and E. coli MG1655 on ASPC-1, Mia-capa-2, and panc-1 cells in accordance with an example embodiment.

The in vitro cytotoxic effects 600 and 602 of *E. coli* SH1 on human cancer cell lines are shown in FIGS. 6A and 6B. FIG. 6A shows that *E. coli* SH1 has cytotoxic effect on SW480 and HCT116 cells, while *E. coli* MG1655 has no significantly cytotoxic effects on these cells. FIG. 6B shows that *E. coli* SH1 has cytotoxic effect on ASPC-1, Mia-capa-2, and panc-1 cells, while *E. coli* MG1655 has no significantly cytotoxic effects on these cells.

EXAMPLE 7

In this example, the inhibitory effects of intravenously injected *E. coli* JYH1 on tumor growth in vivo were evaluated.

Figures 7A, 7B:
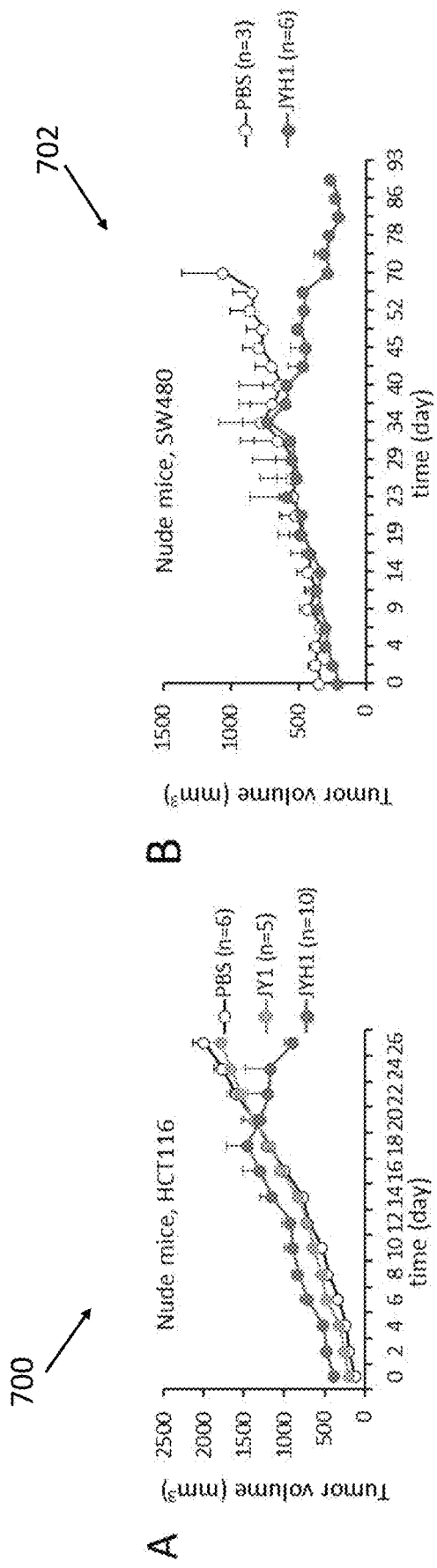
FIG. 7A shows the inhibitory effect of intravenously injected E. coli JYH1 on the growth of HCT 116 tumors in nude mice in accordance with an example embodiment.
FIG. 7B shows the inhibitory effect of intravenously injected E. coli JYH1 on the growth of SW480 tumors in nude mice in accordance with an example embodiment.

FIG. 7A shows the inhibitory effect 700 of intravenously injected *E. coli* JYH1 on the growth of HCT116 tumors in nude mice. Intravenous injection of JYH1 repressed growth of HCT116 tumors in nude mice. In contrast, JY1 had little effects on the tumor growth compared to the PBS control. The HCT116 tumors of JY1-treated mice grew equally well with those of PBS-treated controls, whereas the HCT116 tumors of JYH1-treated mice grew relatively slowly and 50% of them (5 out of 10) started to regress 18-26 days after the intravenous injection of the bacteria ($10^7$/mouse). JYH1 displayed inhibitory effects on HCT116 tumor growth of 100% of the tested mice (n=10), demonstrating a significantly better antitumor efficacy than JY1 (Fisher's Exact test, $p<0.0001$).

Figure 7D:
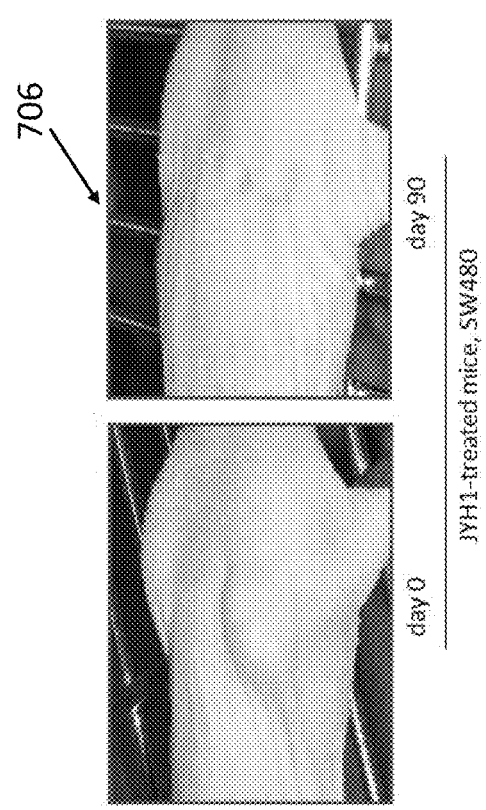
FIG. 7D shows a representative photo of SW480 tumors treated by intravenous injection of JYH 1 in mice from 0-90 days in accordance with an example embodiment.
Figure 7C:
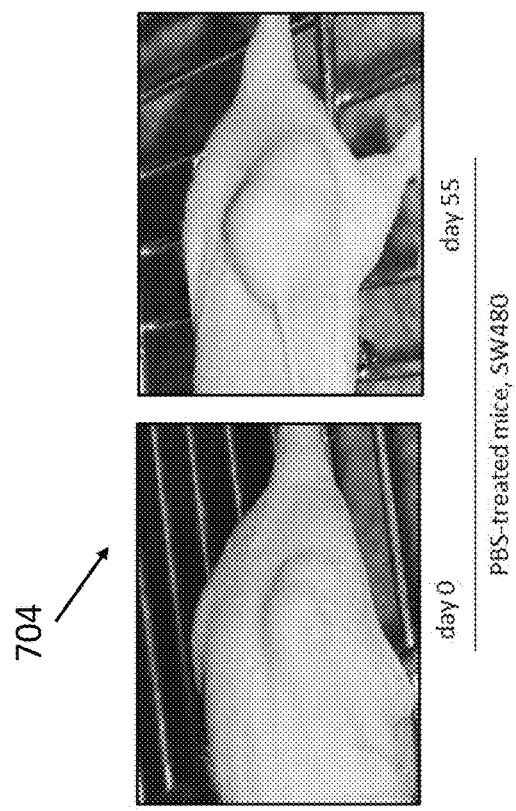
FIG. 7C shows a representative photo of SW480 tumors treated by intravenous injection of PBS in mice from 0-55 days in accordance with an example embodiment.

FIG. 7B shows an analysis 702 for the inhibitory effect of intravenously injected *E. coli* JYH1 on the growth of SW480 tumors in nude mice. FIG. 7C shows representative photos 704 of a SW480 tumor in PBS-treated mice from 0 and 55 days. FIG. 7D shows representative photos 706 of a SW480 tumor in JYH 1-treated mice from 0 and 90 days. Growth of the SW480 tumors was monitored for as long as 90 days. Tumors of the JYH1-treated mice (n=6) regressed 26-52 days after the intravenous injection of JYH1, with the effective percentage being 100%. Among these, tumors of 66.7% of the mice (4 out of 6) disappeared and did not relapse by the end of the experiments. The tumor of one of the remaining two mice was not cured but kept quiescent. The tumor of only one mouse relapsed (16.67%, 1 out of 6). In contrast, none of the PBS-treated tumors regressed or disappeared. These data further showed that JYH1 has significant repressive effects on tumor growth in vivo.

Therefore, in an example embodiment, bacteria that are toxic to both tumor cells and normal tissue cells can become specific to tumors and repress tumor growth without affecting normal tissues, when the bacteria are equipped with the tumor-targeting nucleic acid system.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, "immediately", "immediately upstream" or "immediately downstream", means that there are no other nucleotides between one DNA fragment and another DNA fragment.

As used herein, "system" refers to a combination or a genetic circuit that includes the toxin gene, the antidote gene and their respective promoters. The toxin gene and the antidote gene of the system may be placed in any order. The toxin gene and the antidote gene of the system may be located in the same molecule or in different molecules. In an example embodiment, one of the toxin gene and the antidote gene may be in the chromosome of a bacterium while the other gene may be in a plasmid in the same bacterium.

What is claimed is:

1. A method of constructing a bacterial strain that is genetically engineered, the method comprising:
generating a random library of a nucleic acid system by inserting a random sequence that consists of 5-6 nucleotides to replace original or native nucleotides of the bacterial strain that are located immediately upstream of a second DNA fragment;
inserting, into the bacterial strain, the nucleic acid system that includes:
a first DNA fragment that encodes a toxin gene that expresses a toxin that kills the bacterial strain;
the second DNA fragment that encodes an antidote gene that expresses an antidote that negates the toxin;
a first promoter that controls transcription of the antidote gene, such that glucose represses the transcription of the antidote gene; and
a first constitutive promoter that causes constitutive expression of the toxin gene; and
the random sequence that consists of 5-6 nucleotides and that replaces the original or native 5-6 nucleotides of the bacterial strain located immediately upstream of the second DNA fragment;
culturing clones of the bacterial strain that includes the nucleic acid system; and
selecting the clones that grow in the absence of glucose but do not grow in the presence of glucose at a concentration equal or higher than 1 mM, thereby obtaining the bacteria strain that is genetically engineered and targets solid tumors; and
wherein a pair of the toxin and the antidote is selected from a group consisting of a CcdB-CcdA pair, an AvrRxo1-Arc1 pair, an Hha-TomB pair, and a PaaA2-ParE2 pair.

2. The method of claim 1, wherein the random sequence is GCCTT or TGTCT.

3. The method of claim 1, wherein the clones that grow at a glucose concentration of 0 mM but do not grow at a glucose concentration of 5 mM are selected as the genetically engineered bacteria strain that targets the tumors.

4. The method of claim 1, wherein the second DNA fragment is transcribed at a glucose environment with a concentration lower than 0.424 mM but not transcribed at a glucose environment with a concentration higher than 1.22 mM.

5. The method of claim 1, wherein the bacterial strain is selected from a group consisting of *Escherichia coli*, *Salmonella* and *Shigella*.

6. The method of claim 1, wherein the original or native 5-6 nucleotides are located downstream of the first promoter.

7. The method of claim 1, wherein the first promoter is located immediately upstream of the second DNA fragment.

8. The method of claim 1, wherein the first constitutive promoter is located immediately upstream of the first DNA fragment.

9. The method of claim 1, wherein the first promoter is selected from a group consisting of a lac promoter, a gltA promoter, an sdhADC promoter and a tnaB promoter.

10. The method of claim 1, wherein the first DNA fragment comprises nucleotide sequence SEQ ID NO:1, and the second DNA fragment comprises nucleotide sequence SEQ ID NO:2.

11. The method of claim 1, wherein the first promoter comprises nucleotide sequence SEQ ID NO:3.

12. The method of claim 1, wherein the nucleic acid system further comprises
a third DNA fragment that encodes a chloramphenicol resistance cassette,
wherein the third DNA fragment comprises nucleotide sequence SEQ ID NO:4.

13. The method of claim 1, wherein the bacterial strain is selected from the group consisting of *Escherichia coli* MG1655 and *Escherichia coli* SH1.

14. The method of claim 1, wherein the nucleic acid system comprises a rrnB transcription termination region as shown in nucleotide sequence SEQ ID NO: 6.

15. The method of claim 1, wherein the nucleic acid system comprises nucleotide sequence SEQ ID NO:7 or SEQ ID NO:8.

* * * * *

SEQUENCE LISTING

<160> NUMBER OF SEQ ID NOS: 8

<210> SEQ ID NO 1
<211> LENGTH: 306
<212> TYPE: DNA
<213> ORGANISM: Escherichia coli

<400> SEQUENCE: 1

```
atgcagttta aggtttacac ctataaaaga gagagccgtt atcgtctgtt tgtggatgta    60
cagagtgata ttattgacac gcccgggcga cggatggtga tccccctggc cagtgcacgt   120
ctgctgtcag ataaagtctc ccgtgaactt tacccggtgg tgcatatcgg ggatgaaagc   180
tggcgcatga tgaccaccga tatggccagt gtgccggtct ccgttatcgg ggaagaagtg   240
gctgatctca gccaccgcga aaatgacatc aaaaacgcca ttaacctgat gttctgggga   300
atataa                                                              306
```

<210> SEQ ID NO 2
<211> LENGTH: 219
<212> TYPE: DNA
<213> ORGANISM: Escherichia coli

<400> SEQUENCE: 2

```
atgaagcagc gtattacagt gacagttgac agcgacagct atcagttgct caaggcatat    60
gatgtcaata tctccggtct ggtaagcaca accatgcaga atgaagcccg tcgtctgcgt   120
gccgaacgct ggaaagcgga aaatcaggag gggatggctg aggtcgcccg gtttattgaa   180
atgaacggct cttttgctga tgagaacagg gactggtga                          219
```

<210> SEQ ID NO 3
<211> LENGTH: 164
<212> TYPE: DNA
<213> ORGANISM: Escherichia coli

<400> SEQUENCE: 3

```
taatgcagct ggcacgacag gtttcccgac tggaaagcgg gcagtgagcg caacgcaatt    60
aatgtgagtt agctcactca ttaggcaccc caggctttac actttatgct tccggctcgt   120
atgttgtgtg gaattgtgag cggataacaa tttcacacag gaaa                    164
```

<210> SEQ ID NO 4
<211> LENGTH: 1101
<212> TYPE: DNA
<213> ORGANISM: Escherichia coli

<400> SEQUENCE: 4

```
ataacttcgt ataatgtatg ctatacgaag ttattaggtc tgaagaggag tttacgtcca    60
gccaagctta ggatcccggg taccgatatc ggcagcatca cccgacggac tttgcgccga   120
ataaatacct gtgacggaag atcacttcgc agaataaata atcctggtg tccctgttga   180
taccgggaag ccctgggcca acttttggcg aaaatgagac gttgatcggc acgtaagagg   240
ttccaacttt caccataatg aagtaagatc actaccgggc gtattttttg agttatcgag   300
attttcagga gctaaggaag ctaaaatgga gaaaaaatc actggatata ccaccgttga   360
tatatcccaa tggcatcgta aagaacattt tgaggcattt cagtcagttg ctcaatgtac   420
ctataaccag accgttcagc tggatattac ggcctttta aagaccgtaa agaaaaataa   480
gcacaagttt tatccggcct ttattcacat tcttgcccgc cagatgaatg ctcatccgga   540
attccgtatg gcaatgaaag acggtgagct ggtgatatgg gatagtgttc acccttgtta   600
```

```
caccgttttc catgagcaaa ctgaaacgtt tcatcgctc tggagtgaat accacgacga      660
tttccggcag tttctacaca tatattcgca agatgtggcg tgttacggtg aaaacctggc      720
ctatttccct aaagggttta ttgagaatat gttttcgtc tcagccaatc cctgggtgag      780
tttcaccagt tttgatttaa acgtggccaa tatggacaac ttcttcgccc cgttttcac      840 catgggcaaa tattatacgc aaggcgacaa ggtgctgatg ccgctgacga ttcaggttca      900
tcatgccgtt tgtgatggct tccatgtcgg cagaatgctt aatgaattac aacagtactg      960
cgatgagtgg cagggcgggg cgtaattttt ttaaggcagt tattggtgcc cttagatatc     1020
aagcttagga tccggaaccc ttaatataac ttcgtataat gtatgctata cgaagttatt     1080
aggtccctcg aagaggttca c                                              1101

<210> SEQ ID NO 5
<211> LENGTH: 342
<212> TYPE: DNA
<213> ORGANISM: Escherichia coli

<400> SEQUENCE: 5
aacgcgtgga tccggcttac taaaagccag ataacagtat gcgtatttgc gcgctgattt       60
ttgcggtata agaatatata ctgatatgta tacccgaagt atgtcaaaaa gaggtgtgct      120
atgaagcagc gtattacagt gacagttgac agcgacagct atcagttgct caaggcatat      180
atgatgtcaa tatctccggt ctggtaagca caaccatgca gaatgaagcc cgtcgtctgc      240
gtgccgaacg ctggaaagcg gaaaatcagg aagggatggc tgaggtcgcc cggtttattg      300
aaatgaacgg ctcttttgct gacgagaaca gggactggtg aa                        342

<210> SEQ ID NO 6
<211> LENGTH: 158
<212> TYPE: DNA
<213> ORGANISM: Escherichia coli

<400> SEQUENCE: 6
tgcctggcgg cagtagcgcg gtggtccac ctgaccccat gccgaactca gaagtgaaac       60
gccgtagcgc cgatggtagt gtggggtctc cccatgcgag agtagggaac tgccaggcat     120
caaataaaac gaaaggctca gtcgaaagac tgggcctt                            158

<210> SEQ ID NO 7
<211> LENGTH: 2710
<212> TYPE: DNA
<213> ORGANISM: Artificial Sequence
<220> FEATURE:
<223> OTHER INFORMATION: nucleic acid system of one example embodiment

<400> SEQUENCE: 7
aacgcgtgga tccggcttac taaaagccag ataacagtat gcgtatttgc gcgctgattt       60
ttgcggtata agaatatata ctgatatgta tacccgaagt atgtcaaaaa gaggtgtgct      120
atgaagcagc gtattacagt gacagttgac agcgacagct atcagttgct caaggcatat      180
atgatgtcaa tatctccggt ctggtaagca caaccatgca gaatgaagcc cgtcgtctgc      240
gtgccgaacg ctggaaagcg gaaaatcagg aagggatggc tgaggtcgcc cggtttattg      300
aaatgaacgg ctcttttgct gacgagaaca gggactggtg aaatgcagtt taaggtttac      360
acctataaaa gagagagccg ttatcgtctg tttgtggatg tacagagtga tattattgac      420
acgcccgggc gacggatggt gatccccctg gccagtgcac gtctgctgtc agataaagtc      480
```

```
tcccgtgaac tttacccggt ggtgcatatc ggggatgaaa gctggcgcat gatgaccacc      540
gatatggcca gtgtgccggt ctccgttatc ggggaagaag tggctgatct cagccaccgc      600
gaaaatgaca tcaaaaacgc cattaacctg atgttctggg aatataaat gtcaggctcc       660 gttatacaca gccagtctgc aggtcgacca tagtgactgg atatgttgtg ttttacagta      720
ttatgtagtc tgttttttat gcaaaatcta atttaatata ttgatattta tatcatttta     780
cgtttctcgt tcagctttct tgtacaaagt ggtgatcaag cttgaaggta agcctatccc      840
taaccctctc ctcggtctcg attctacgcg taccggtcat catcaccatc accattgagt      900
ttaaacggtc tccagcttgg ctgttttggc ggatgagaga agattttcag cctgatacag      960
attaaatcag aacgcagaag cggtctgata aacagaatt tgcctggcgg cagtagcgcg      1020
gtggtcccac ctgaccccat gccgaactca gaagtgaaac gccgtagcgc cgatggtagt      1080
gtggggtctc cccatgcgag agtagggaac tgccaggcat caaataaaac gaaaggctca     1140
gtcgaaagac tgggccttaa taggcgtatc acgaggccct ttcgtcttca agaattccga     1200
tcatattcaa taaccttaa tataacttcg tataatgtat gctatacgaa gttattaggt      1260
ctgaagagga gtttacgtcc agccaagctt aggatcccgg gtaccgatat cggcagcatc     1320
acccgacgga ctttgcgccg aataaatacc tgtgacggaa gatcacttcg cagaataaat     1380
aaatcctggt gtccctgttg ataccgggaa gccctgggcc aacttttggc gaaaatgaga    1440
cgttgatcgg cacgtaagag gttccaactt tcaccataat gaagtaagat cactaccggg    1500
cgtatttttt gagttatcga gattttcagg agctaaggaa gctaaatgg agaaaaaaat    1560 cactggatat accaccgttg atatatccca atggcatcgt aaagaacatt ttgaggcatt   1620
tcagtcagtt gctcaatgta cctataacca gaccgttcag ctggatatta cggcctttttt  1680 aaagaccgta agaaaaaata agcacaagtt ttatccggcc tttattcaca ttcttgcccg   1740
ccagatgaat gctcatccgg aattccgtat ggcaatgaaa gacggtgagc tggtgatatg   1800
ggatagtgtt cacccttgtt acaccgtttt ccatgagcaa actgaaacgt tttcatcgct   1860
ctggagtgaa taccacgacg atttccggca gtttctacac atatattcgc aagatgtggc   1920
gtgttacggt gaaaacctgg cctatttccc taaagggttt attgagaata tgttttcgt   1980 ctcagccaat ccctgggtga gtttcaccag ttttgattta aacgtggcca atatggacaa   2040
cttcttcgcc cccgttttca ccatgggcaa atattatacg caaggcgaca aggtgctgat   2100
gccgctgacg attcaggttc atcatgccgt ttgtgatggc ttccatgtcg cagaatgct   2160 taatgaatta caacagtact gcgatgagtg cagggcggg gcgtaatttt tttaaggcag   2220
ttattggtgc ccttagatat caagcttagg atccggaacc cttaatataa cttcgtataa   2280
tgtatgctat acgaagttat taggtccctc gaagaggttc actaatgcag ctggcacgac   2340
aggtttcccg actggaaagc gggcagtgag cgcaacgcaa ttaatgtgag ttagctcact   2400
cattaggcac cccaggcttt acactttatg cttccggctc gtatgttgtg tggaattgtg   2460
agcggataac aatttcacac aggaaatgtc tatgaagcag cgtattacag tgacagttga   2520
cagcgacagc tatcagttgc tcaaggcata tgatgtcaat atctccggtc tggtaagcac   2580
aaccatgcaa aatgaagccc gtcgtctgcg tgccgaacgc tggaaagcgg aaaatcagga   2640
ggggatggct gaggtcgccc ggtttattga atgaacggc tcttttgctg atgagaacag    2700
ggactggtga                                                             2710
```

<210> SEQ ID NO 8
<211> LENGTH: 2710

<212> TYPE: DNA
<213> ORGANISM: Artificial Sequence
<220> FEATURE:
<223> OTHER INFORMATION: Nucleic acid system of another example
    embodiment

<400> SEQUENCE: 8

```
aacgcgtgga tccggcttac taaaagccag ataacagtat gcgtatttgc gcgctgattt     60
ttgcggtata agaatatata ctgatatgta tacccgaagt atgtcaaaaa gaggtgtgct    120
atgaagcagc gtattacagt gacagttgac agcgacagct atcagttgct caaggcatat    180
atgatgtcaa tatctccggt ctggtaagca caaccatgca gaatgaagcc cgtcgtctgc    240
gtgccgaacg ctggaaagcg gaaaatcagg aagggatggc tgaggtcgcc cggtttattg    300
aaatgaacgg ctcttttgct gacgagaaca gggactggtg aaatgcagtt aaggtttac     360
acctataaaa gagagagccg ttatcgtctg tttgtggatg tacagagtga tattattgac    420
acgcccgggc gacggatggt gatcccctg gccagtgcac gtctgctgtc agataaagtc     480
tcccgtgaac tttacccggt ggtgcatatc ggggatgaaa gctggcgcat gatgaccacc    540
gatatggcca gtgtgccggt ctccgttatc ggggaagaag tggctgatct cagccaccgc    600
gaaaatgaca tcaaaaacgc cattaacctg atgttctggg aatataaat gtcaggctcc     660
gttatacaca gccagtctgc aggtcgacca tagtgactgg atatgttgtg ttttacagta    720
ttatgtagtc tgtttttat gcaaaatcta atttaatata ttgatattta tatcatttta    780
cgtttctcgt tcagctttct tgtacaaagt ggtgatcaag cttgaaggta agcctatccc    840
taaccctctc ctcggtctcg attctacgcg taccggtcat catcaccatc accattgagt    900
ttaaacggtc tccagcttgg ctgttttggc ggatgagaga agattttcag cctgatacag    960
attaaatcag aacgcagaag cggtctgata aaacagaatt tgcctggcgg cagtagcgcg   1020
gtggtcccac ctgaccccat gccgaactca gaagtgaaac gccgtagcgc cgatggtagt   1080
gtggggtctc cccatgcgag agtagggaac tgccaggcat caaataaaac gaaaggctca   1140
gtcgaaagac tgggccttaa taggcgtatc acgaggccct ttcgtcttca agaattccga   1200
tcatattcaa taaccccttaa tataacttcg tataatgtat gctatacgaa gttattaggt   1260
ctgaagagga gtttacgtcc agccaagctt aggatcccgg gtaccgatat cggcagcatc   1320
acccgacgga ctttgcgccg aataaatacc tgtgacggaa gatcacttcg cagaataaat   1380
aaatcctggt gtccctgttg ataccgggaa gccctgggcc aacttttggc gaaaatgaga   1440
cgttgatcgg cacgtaagag gttccaactt tcaccataat gaagtaagat cactaccggg   1500
cgtatttttt gagttatcga gattttcagg agctaaggaa gctaaaatgg agaaaaaaat   1560
cactggatat accaccgttg atatatccca atggcatcgt aaagaacatt ttgaggcatt   1620
tcagtcagtt gctcaatgta cctataacca gaccgttcag ctggatatta cggcctttttt  1680
aaagaccgta agaaaaata agcacaagtt ttatccggcc tttattcaca ttcttgcccg   1740
ccagatgaat gctcatccgg aattccgtat ggcaatgaaa gacggtgagc tggtgatatg   1800
ggatagtgtt cacccttgtt acaccgtttt ccatgagcaa actgaaacgt tttcatcgct   1860
ctggagtgaa taccacgacg atttccggca gtttctacac atatattcgc aagatgtggc   1920
gtgttacggt gaaaacctgg cctatttccc taaagggttt attgagaata tgttttttcgt 1980
ctcagccaat ccctgggtga gtttcaccag ttttgattta acgtggcca atatggacaa    2040
cttcttcgcc cccgttttca ccatgggcaa atattacg caaggcgaca aggtgctgat      2100
gccgctgacg attcaggttc atcatgccgt ttgtgatggc ttccatgtcg gcagaatgct   2160
```

```
taatgaatta caacagtact gcgatgagtg gcagggcggg gcgtaatttt tttaaggcag    2220
ttattggtgc ccttagatat caagcttagg atccggaacc cttaatataa cttcgtataa    2280
tgtatgctat acgaagttat taggtccctc gaagaggttc actaatgcag ctggcacgac    2340
aggtttcccg actggaaagc gggcagtgag cgcaacgcaa ttaatgtgag ttagctcact    2400
cattaggcac cccaggcttt acactttatg cttccggctc gtatgttgtg tggaattgtg    2460
agcggataac aatttcacac aggaaagcct tatgaagcag cgtattacag tgacagttga    2520
cagcgacagc tatcagttgc tcaaggcata tgatgtcaat atctccggtc tggtaagcac    2580
aaccatgcag aatgaagccc gtcgtctgcg tgccgaacgc tggaaagcgg aaaatcagga    2640
ggggatggct gaggtcgccc ggtttattga aatgaacggc tcttttgctg atgagaacag    2700
ggactggtga                                                           2710
```